US012774453B2

(12) United States Patent
Cusumano et al.

(10) Patent No.: US 12,774,453 B2
(45) Date of Patent: Oct. 27, 2026

(54) METHODS FOR USING PHYTASE IN ETHANOL PRODUCTION

(71) Applicant: DANSTAR FERMENT AG, Zug (CH)

(72) Inventors: Danielle Cusumano, San Diego, CA (US); Tony Newton, San Diego, CA (US); Arne I. Solbak, San Diego, CA (US)

(73) Assignee: DANSTAR FERMENT AG, Zug (CH)

( * ) Notice: Subject to any disclaimer, the term of this patent is extended or adjusted under 35 U.S.C. 154(b) by 753 days.

(21) Appl. No.: 17/932,474

(22) Filed: Sep. 15, 2022

(65) Prior Publication Data

US 2023/0121286 A1 Apr. 20, 2023

Related U.S. Application Data

(62) Division of application No. 16/082,079, filed as application No. PCT/US2017/020592 on Mar. 3, 2017, now Pat. No. 11,447,757.

(60) Provisional application No. 62/305,439, filed on Mar. 8, 2016.

(51) Int. Cl.

| | |
|---|---|
| ***C12N 9/16*** | (2006.01) |
| ***C12C 5/00*** | (2006.01) |
| ***C12C 11/00*** | (2006.01) |
| ***C12G 3/02*** | (2019.01) |
| ***C12P 7/12*** | (2006.01) |

(52) U.S. Cl.

CPC ................ *C12N 9/16* (2013.01); *C12C 5/004* (2013.01); *C12C 11/00* (2013.01); *C12G 3/02* (2013.01); *C12P 7/12* (2013.01); *C12Y 301/03* (2013.01)

(58) Field of Classification Search

CPC ... C12Y 301/03008; C12P 7/06; A23K 10/12; C12N 9/16

See application file for complete search history.

(56) References Cited

U.S. PATENT DOCUMENTS

| | | | |
|---|---|---|---|
| 5,536,325 A | 7/1996 | Brink | |
| 6,183,740 B1 | 2/2001 | Short et al. | |
| 6,423,145 B1 | 7/2002 | Nguyen et al. | |
| 6,660,506 B2 | 12/2003 | Nguyen et al. | |
| 6,855,365 B2 | 2/2005 | Short et al. | |
| 8,936,924 B2 | 1/2015 | Solbak et al. | |
| 11,447,757 B2 * | 9/2022 | Cusumano | C12G 3/02 |
| 2002/0164730 A1 | 11/2002 | Perdices et al. | |
| 2004/0091968 A1 | 5/2004 | Short et al. | |
| 2005/0069998 A1 | 3/2005 | Perdices et al. | |
| 2006/0014260 A1 | 1/2006 | Fan et al. | |
| 2010/0000719 A1 | 1/2010 | Romer et al. | |
| 2015/0267225 A1 | 9/2015 | Bazzana et al. | |

FOREIGN PATENT DOCUMENTS

| | | |
|---|---|---|
| CN | 103502443 A | 1/2014 |
| CN | 104805025 A | 7/2015 |
| WO | WO-8100857 A1 | 4/1981 |
| WO | WO-0043496 A1 | 7/2000 |
| WO | WO-0162947 A1 | 8/2001 |
| WO | 01/89317 A2 | 11/2001 |
| WO | 2004/015084 A2 | 2/2004 |
| WO | WO-2005096804 A2 | 10/2005 |
| WO | 2009/052275 A1 | 4/2009 |
| WO | 2011/117406 A1 | 9/2011 |
| WO | WO-2012143862 A1 | 10/2012 |
| WO | WO-2015197871 A1 | 12/2015 |

OTHER PUBLICATIONS

Partial Supplementary European Search Report for EP Patent Application No. 17763783.2, issued on Jul. 9, 2019, five (5) pages.

Gonzalez, et al. "Production of ethanol from thin stillage by metabolically engineered *Escherichia coli*," *Biotechnology Letters* 32(3):405-411 (Nov. 2009).

Liu, J., et al. "Influence on the fermentation with different raw corn flour by applying phytase," *Chemical Engineer* 9:70-72, (Sep. 2014).

* cited by examiner

*Primary Examiner* — Tekchand Saidha

(74) *Attorney, Agent, or Firm* — STERNE, KESSLER, GOLDSTEIN & FOX P.L.L.C.

(57) ABSTRACT

The present disclosure relates to methods for using one or more polypeptides with phytase activity in grain processing, ethanol, and biofuel production.

18 Claims, 7 Drawing Sheets

Specification includes a Sequence Listing.

Average Yeast Cell Count

Baseline Novo 50161 B# 1539 - 1566, 1814 PPM Phosphate as PO4-3 @ 21.5 hrs

| Time (h) | 8.1 | 12.5 | 20 | 30 | 40 | 50 | 60.1 | 69.3 | 86.3 |
|---|---|---|---|---|---|---|---|---|---|
| Start Date | AYCC | AYCC | AYCC | AYCC | AYCC | AYCC | AYCC | AYCC | AYCC |
| Average | 357 | 275 | 296 | 295 | 298 | | | | |
| STD DEV | 47 | 54 | 35 | 27 | 39 | | | | |

Verenium Phytase B B# 1567 - 1595, 2039 PPM Phosphate as PO4-3 @ 28.3 hrs

| Time (h) | 8.1 | 13.9 | 20.5 | 30 | 40.3 | 50.4 | 59.8 | 69.3 | 83.7 |
|---|---|---|---|---|---|---|---|---|---|
| Start Date | AYCC | AYCC | AYCC | AYCC | AYCC | AYCC | AYCC | AYCC | AYCC |
| Average | 327 | 295 | 287 | 292 | 303 | | | | |
| STD DEV | 44 | 36 | 49 | 35 | 37 | | | | |

PhytOUT B# 1059 - 1086, 1603 PPM Phosphate as PO4-3 @ 26.6 hrs

| Time (h) | 8.4 | 11.8 | 20.5 | 29.7 | 40.4 | 50.4 | 60.2 | 67.3 | |
|---|---|---|---|---|---|---|---|---|---|
| Start Date | AYCC | AYCC | AYCC | AYCC | AYCC | AYCC | AYCC | AYCC | AYCC |
| Average | 333 | 197 | 240 | 238 | 248 | | | | |
| STD DEV | 30 | 40 | 33 | 36 | 34 | | | | |

Non-Phytase B# 947 - 949, 944 PPM Phosphate as PO4-3 @ 65 hrs

| Time (h) | 8.8 | 10.8 | 19.0 | 32.0 | 39.1 | 50.1 | 61.9 | | |
|---|---|---|---|---|---|---|---|---|---|
| Start Date | AYCC | AYCC | AYCC | AYCC | AYCC | AYCC | AYCC | AYCC | AYCC |
| Average | 396 | 156 | 234 | 229 | 270 | | | | |
| STD DEV | | | 25.16 | | 9.19 | | | | |

Average Yeast Cell Count by data set

| | Novo 50161 AYCC | Phytase B AYCC | PhytOUT AYCC | Non-Phytase AYCC |
|---|---|---|---|---|
| Average | 304 | 301 | 251 | 257 |

Fig. 2a

Average % Yeast Budding

Baseline Novo 50161 B# 1539 - 1566, 1814 PPM Phosphate as PO4-3 @ 21.5 hrs

| | | | | | | | | | |
|---|---|---|---|---|---|---|---|---|---|
| Time (h) | 8.1 | 12.5 | 20 | 30 | 40 | 50 | 60.1 | 69.3 | 86.3 |
| Start Date | BUD | BUD | BUD | BUD | BUD | BUD | BUD | BUD | BUD |
| Average | 21.7 | 20.2 | 18.1 | 16.5 | 25.2 | | | | |
| STD DEV | 3.8 | 4.4 | 3.3 | 3.3 | 24.3 | | | | |

Verenium Phytase B B# 1567 - 1595, 2039 PPM Phosphate as PO4-3 @ 28.3 hrs

| | | | | | | | | | |
|---|---|---|---|---|---|---|---|---|---|
| Time (h) | 8.1 | 13.9 | 20.5 | 30 | 40.3 | 50.4 | 59.8 | 69.3 | 83.7 |
| Start Date | BUD | BUD | BUD | BUD | BUD | BUD | BUD | BUD | BUD |
| Average | 28.9 | 32.7 | 24.5 | 18.7 | 20.6 | | | | |
| STD DEV | 7.8 | 8.6 | 7.5 | 3.8 | 3.3 | | | | |

PhytOUT B# 1059 - 1086, 1603 PPM Phosphate as PO4-3 @ 26.6 hrs

| | | | | | | | | | |
|---|---|---|---|---|---|---|---|---|---|
| Time (h) | 8.4 | 11.8 | 20.5 | 29.7 | 40.4 | 50.4 | 60.2 | 67.3 | |
| Start Date | BUD | BUD | BUD | BUD | BUD | BUD | BUD | BUD | BUD |
| Average | 24.6 | 22.6 | 20.5 | 20.1 | 20.4 | | | | |
| STD DEV | 3.4 | 4.5 | 4.2 | 3.6 | 4.5 | | | | |

Non-Phytase B# 947 - 949, 944 PPM Phosphate as PO4-3 @ 65 hrs

| | | | | | | | | | |
|---|---|---|---|---|---|---|---|---|---|
| Time (h) | 8.8 | 10.8 | 19.0 | 32.0 | 39.1 | 50.1 | 61.9 | | |
| Start Date | BUD | BUD | BUD | BUD | BUD | BUD | BUD | BUD | BUD |
| Average | 25.0 | 29.0 | 27.3 | 25.0 | 26.0 | | | | |
| STD DEV | | | 2.9 | | 2.8 | | | | |

Average % budding by data set

| | Novo 50161 Budding % | Phytase B Budding % | PhytOUT Budding 5 | Non-Phytase Budding % |
|---|---|---|---|---|
| Average | 20 | 25 | 22 | 26 |

Fig. 2b

Average % Yeast Viability

Baseline Novo 50161 B# 1539 - 1566, 1814 PPM Phosphate as PO4-3 @ 21.5 hrs

| Time (h) | 8.1 | 12.5 | 20 | 30 | 40 | 50 | 60.1 | 69.3 | 86.3 |
|---|---|---|---|---|---|---|---|---|---|
| Start Date | VIA | VIA | VIA | VIA | VIA | VIA | VIA | VIA | VIA |
| Average | 97.44 | 96.79 | 95.60 | 96.91 | 89.05 | | | | |
| STD DEV | 2.29 | 3.40 | 3.30 | 2.64 | 23.47 | | | | |

Verenium Phytase B B# 1567 - 1595, 2039 PPM Phosphate as PO4-3 @ 28.3 hrs

| Time (h) | 8.1 | 13.9 | 20.5 | 30 | 40.3 | 50.4 | 59.8 | 69.3 | 83.7 |
|---|---|---|---|---|---|---|---|---|---|
| Start Date | VIA | VIA | VIA | VIA | VIA | VIA | VIA | VIA | VIA |
| Average | 96.91 | 99.00 | 97.43 | 97.93 | 98.83 | | | | |
| STD DEV | 3.72 | 2.00 | 3.13 | 2.28 | 1.95 | | | | |

PhytOUT B# 1059 - 1086, 1603 PPM Phosphate as PO4-3 @ 26.6 hrs

| Time (h) | 8.4 | 11.8 | 20.5 | 29.7 | 40.4 | 50.4 | 60.2 | 67.3 | |
|---|---|---|---|---|---|---|---|---|---|
| Start Date | VIA | VIA | VIA | VIA | VIA | VIA | VIA | VIA | VIA |
| Average | 97.00 | 96.63 | 96.45 | 96.13 | 95.96 | | | | |
| STD DEV | 1.27 | 1.31 | 1.44 | 1.46 | 1.78 | | | | |

Non-Phytase B# 947 - 949, 944 PPM Phosphate as PO4-3 @ 65 hrs

| Time (h) | 8.8 | 10.8 | 19.0 | 32.0 | 39.1 | 50.1 | 61.9 | | |
|---|---|---|---|---|---|---|---|---|---|
| Start Date | VIA | VIA | VIA | VIA | VIA | VIA | VIA | VIA | VIA |
| Average | 98.00 | 96.00 | 97.67 | 98.00 | 96.50 | | | | |
| STD DEV | | | 0.58 | | 0.71 | | | | |

Average % viability by data set

| | Novo 50161 % Viability | Phytase B % Viability | PhytOUT % Viability | Non-Phytase % Viability |
|---|---|---|---|---|
| Average | 95.2 | 98.0 | 96.4 | 97.2 |

Fig. 2c

Ethanol Yields

Baseline Novo 50161 B# 1539 - 1566, 1814 PPM Phosphate as PO4-3 @ 21.5 hrs.

| Time (h) | 8.0 | 12.5 | 20.0 | 29.9 | 39.6 | 49.7 | 60.0 | 69.1 | |
|---|---|---|---|---|---|---|---|---|---|
| Start Date | ETOH | ETOH | ETOH | ETOH | ETOH | ETOH | ETOH | ETOH | ETOH |
| Average | 2.89 | 3.65 | 6.65 | 9.98 | 12.28 | 14.01 | 15.05 | 15.50 | |
| STD DEV | 0.44 | 0.46 | 1.31 | 0.90 | 0.70 | 0.53 | 0.32 | 0.19 | |

Verenium Phytase B B# 1567 - 1595, 2039 PPM Phosphate as PO4-3 @ 28.3 hrs.

| Time (h) | 8.1 | 13.9 | 20.5 | 30 | 40.3 | 50.4 | 59.8 | 69.3 | 83.7 |
|---|---|---|---|---|---|---|---|---|---|
| Start Date | ETOH | ETOH | ETOH | ETOH | ETOH | ETOH | ETOH | ETOH | ETOH |
| Average | 2.75 | 4.04 | 6.59 | 9.82 | 12.16 | 13.96 | 15.09 | 15.56 | 15.75 |
| STD DEV | 0.35 | 0.82 | 1.17 | 0.78 | 0.74 | 1.82 | 0.31 | 0.16 | 0.16 |

PhytOUT B# 1059 - 1086, 1603 PPM Phosphate as PO4-3 @ 26.6 hrs.

| Time (h) | 8.4 | 11.8 | 20.5 | 29.7 | 40.4 | 50.4 | 60.2 | 67.3 | |
|---|---|---|---|---|---|---|---|---|---|
| Start Date | ETOH | ETOH | ETOH | ETOH | ETOH | ETOH | ETOH | ETOH | ETOH |
| Average | 2.85 | 3.12 | 6.63 | 9.48 | 11.79 | 13.37 | 14.40 | 14.74 | |
| STD DEV | 0.29 | 0.63 | 1.22 | 0.72 | 0.65 | 0.54 | 0.33 | 0.29 | |

Non-Phytase B# 947 - 949, 944 PPM Phosphate as PO4-3 @ 65 hrs.

| Time (h) | 8.8 | 10.8 | 19.0 | 32.0 | 39.1 | 50.1 | 61.9 | | |
|---|---|---|---|---|---|---|---|---|---|
| Start Date | ETOH | ETOH | ETOH | ETOH | ETOH | ETOH | ETOH | ETOH | ETOH |
| Average | 3.13 | 2.61 | 5.83 | 10.02 | 11.67 | 13.60 | 14.39 | | |
| STD DEV | 0.51 | 0.38 | 1.74 | 0.75 | 0.60 | 0.29 | 0.26 | | |

Fig. 3a

Glycerol Levels

Baseline Novo 50161 B# 1539 - 1566, 1814 PPM Phosphate as PO4-3 @ 21.5 hrs.

| Time (h) | 8.0 | 12.5 | 20.0 | 29.9 | 39.6 | 49.7 | 60.0 | 69.1 | |
|---|---|---|---|---|---|---|---|---|---|
| Start Date | GLY | GLY | GLY | GLY | GLY | GLY | GLY | GLY | GLY |
| Average | 0.35 | 0.57 | 0.79 | 1.03 | 1.13 | 1.19 | 1.23 | 1.25 | |
| STD DEV | 0.05 | 0.05 | 0.16 | 0.07 | 0.05 | 0.05 | 0.06 | 0.05 | |

Verenium Phytase B B# 1567 - 1595, 2039 PPM Phosphate as PO4-3 @ 28.3 hrs.

| Time (h) | 8.1 | 13.9 | 20.5 | 30 | 40.3 | 50.4 | 59.8 | 69.3 | 83.7 |
|---|---|---|---|---|---|---|---|---|---|
| Start Date | GLY | GLY | GLY | GLY | GLY | GLY | GLY | GLY | GLY |
| Average | 0.33 | 0.58 | 0.78 | 1.00 | 1.10 | 1.16 | 1.20 | 1.22 | 1.21 |
| STD DEV | 0.04 | 0.06 | 0.09 | 0.06 | 0.05 | 0.14 | 0.05 | 0.05 | 0.05 |

PhytOUT B# 1059 - 1086, 1603 PPM Phosphate as PO4-3 @ 26.6 hrs.

| Time (h) | 8.4 | 11.8 | 20.5 | 29.7 | 40.4 | 50.4 | 60.2 | 67.3 | |
|---|---|---|---|---|---|---|---|---|---|
| Start Date | GLY | GLY | GLY | GLY | GLY | GLY | GLY | GLY | GLY |
| Average | 0.35 | 0.50 | 0.78 | 0.96 | 1.06 | 1.11 | 1.13 | 1.12 | |
| STD DEV | 0.03 | 0.07 | 0.09 | 0.05 | 0.06 | 0.05 | 0.05 | 0.05 | |

Non-Phytase B# 947 - 949, 944 PPM Phosphate as PO4-3 @ 65 hrs.

| Time (h) | 8.8 | 10.8 | 19.0 | 32.0 | 39.1 | 50.1 | 61.9 | | |
|---|---|---|---|---|---|---|---|---|---|
| Start Date | GLY | GLY | GLY | GLY | GLY | GLY | GLY | GLY | GLY |
| Average | 0.33 | 0.36 | 0.61 | 0.89 | 0.96 | 1.00 | 1.02 | | |
| STD DEV | 0.05 | 0.06 | 0.13 | 0.03 | 0.03 | 0.02 | 0.01 | | |

Fig. 3b

Total Sugar Levels

Baseline Novo 50161 B# 1539 - 1566, 1814 PPM Phosphate as PO4-3 @ 21.5 hrs.

| Time (h) | 8.0 | 12.5 | 20.0 | 29.9 | 39.6 | 49.7 | 60.0 | 69.1 | |
|---|---|---|---|---|---|---|---|---|---|
| Start Date | TS | TS | TS | TS | TS | TS | TS | TS | TS |
| Average | 6.24 | 25.00 | 19.69 | 11.08 | 6.35 | 3.61 | 1.80 | 1.16 | |
| STD DEV | 1.36 | 2.21 | 3.44 | 2.29 | 1.24 | 1.02 | 0.66 | 0.36 | |

Verenium Phytase B B# 1567 - 1595, 2039 PPM Phosphate as PO4-3 @ 28.3 hrs.

| Time (h) | 8.1 | 13.9 | 20.5 | 30 | 40.3 | 50.4 | 59.8 | 69.3 | 83.7 |
|---|---|---|---|---|---|---|---|---|---|
| Start Date | TS | TS | TS | TS | TS | TS | TS | TS | TS |
| Average | 6.99 | 26.87 | 20.54 | 12.30 | 6.81 | 3.79 | 1.88 | 1.01 | 0.92 |
| STD DEV | 1.04 | 1.80 | 2.97 | 2.32 | 1.30 | 1.92 | 0.53 | 0.10 | 0.06 |

PhytOUT B# 1059 - 1086, 1603 PPM Phosphate as PO4-3 @ 26.6 hrs.

| Time (h) | 8.4 | 11.8 | 20.5 | 29.7 | 40.4 | 50.4 | 60.2 | 67.3 | |
|---|---|---|---|---|---|---|---|---|---|
| Start Date | TS | TS | TS | TS | TS | TS | TS | TS | TS |
| Average | 8.47 | 26.39 | 18.44 | 10.66 | 6.18 | 3.16 | 1.49 | 1.08 | |
| STD DEV | 0.88 | 2.43 | 3.17 | 2.19 | 1.21 | 1.12 | 0.66 | 0.60 | |

Non-Phytase B# 947 - 949, 944 PPM Phosphate as PO4-3 @ 65 hrs.

| Time (h) | 8.8 | 10.8 | 19.0 | 32.0 | 39.1 | 50.1 | 61.9 | | |
|---|---|---|---|---|---|---|---|---|---|
| Start Date | TS | TS | TS | TS | TS | TS | TS | TS | TS |
| Average | 5.21 | 26.92 | 19.53 | 8.13 | 5.21 | 1.94 | 1.00 | | |
| STD DEV | 1.28 | 2.88 | 4.51 | 1.31 | 0.78 | 0.83 | 0.15 | | |

Fig. 3c

METHODS FOR USING PHYTASE IN ETHANOL PRODUCTION

SEQUENCE LISTING

This application includes a nucleotide and amino acid sequence listing in a standardized electronic format (a "Sequence Listing XML") and comply with the rules for submission of a "Sequence Listing XML" in accordance with 37 CFR 1.831 through 1.835 and according to "Recommended Standard For The Presentation of Nucleotide and Amino Acid Sequence Listing Using XML (Extensible Markup Language)" ST.26. The sequence listing, which was created on Sep. 14, 2022, is named "160169US04_SequenceListing_ForFiling," and is hereby incorporated by reference into the specification of this application in its entirety and for all purposes.

FIELD

The present disclosure relates to methods for using one or more polypeptides with phytase activity in grain processing, ethanol, and biofuel production.

BACKGROUND

Conversion of biomass sources such as grains, corn, wheat, or sugarcane into ethanol, biofuels, or biobased products is a rapidly growing industry. Ethanol demand has grown over the last decade for a variety of reasons including regulatory requirements for cleaner burning fuels, such as gasoline/ethanol blends ranging from E10 (a blend with about 10% ethanol) up to E85 (a blend with about 85% ethanol). However, increased vehicle fuel efficiency and economic uncertainty pose future risks for the ethanol production industry unless further improvements in the efficiency and cost-effectiveness of ethanol production are made.

In ethanol production, the multi-step fermentation process used to convert biomass into ethanol produces a large number of byproducts, such as oils, dried distillers grains (DDGs), or dried distillers grains with solubles (DDGS). Some of these byproducts, such as "thin stillage" (a byproduct rich in carbon sources such as glycerol, glucose, and maltose) may be further processed to extract commercially valuable components such as additional ethanol. Gonzalez, et al. "Production of ethanol from thin stillage by metabolically engineered *Escherichia coli*." Biotechnology Letters 2010, 32(3): 405-411. Other byproducts, such as "beerstone" or other organometallic salts, precipitate in ethanol processing equipment and inhibit the proper functioning of such equipment. Removing these problematic byproducts can be a time-consuming or costly process and lead to frequent equipment cleaning or maintenance downtime.

SUMMARY

Some embodiments disclosed herein provide methods for improving efficiency of ethanol production by yeast, the methods comprising (a) providing a variant polypeptide comprising an amino acid sequence that is at least 85% identical to the amino acid sequence as set forth in amino acid residues 23-434 of SEQ ID NO: 2 or that is at least 85% identical to the amino acid sequence as set forth in SEQ ID NO: 3; wherein said variant polypeptide has phytase activity; and (b) adding the variant polypeptide to an ethanol processing fluid in an ethanol production facility, wherein addition of the variant polypeptide improves ethanol production efficiency. The improved ethanol production efficiency comprises one or more of increased yeast cell count, yeast budding or yeast viability; increased ethanol yield, decreased glycerol levels, or decreased total sugar levels; decreased fouling rate; increased phosphorous levels; and increased operation time of the ethanol production facility.

In some embodiments, the ethanol production facility comprises a feedstock, a hammer mill, a slurry tank, a jet cooker, a liquefaction, a mash cooker, a yeast mix tank, a yeast propagator, a fermentation tank, a beer, a distillation system, a whole stillage, a centrifuge, a thin stillage, an evaporator, a condensate, a syrup, a wet grain, a drum dryer, a dried distiller's grains with solubles, a condensed distiller's solubles, a dried distiller's grain, a wet distiller's grains with solubles, or any combination thereof.

In some embodiments, addition of the variant polypeptide improves ethanol production efficiency compared to a production process where no phytase is added. In some embodiments, the addition of the variant polypeptide improves ethanol production efficiency compared to a production process where a wild-type phytase is added. In some embodiments, the addition of the variant polypeptide improves ethanol production efficiency compared to a production process where a commercially available phytase is added.

A variant polypeptide with phytase activity may be added to the ethanol processing fluid at any step of the ethanol production. In some embodiments, the variant polypeptide is added to the ethanol processing fluid prior to fermentation. In some embodiments, the variant polypeptide is added to the ethanol processing fluid in a mash cooker. In some embodiments, the variant polypeptide is added to the ethanol processing fluid in a yeast mix tank. In some embodiments, the ethanol processing fluid proceeds from the yeast mix tank to a yeast propagator. In some embodiments, the variant polypeptide is added at a dose of 0.5 gallons per yeast propagator.

In some embodiments, the decreased fouling rate comprises fouling rate in one or more of beer/mash heat exchanger inlet pressure, beer feed temperature, and beer feed valve position. In some embodiments, the operation time comprises one or both of beer/mash heat exchanger online time and beer feed pre-heater exchanger online time.

In some embodiments, the commercially available phytase is selected from Novozyme 50161 and U.S. Water PhytOUT. In some embodiments, the ethanol production facility is in an ethanol production plant; a spirit or a drinkable alcohol production plant; or a fuel ethanol plant. In some embodiments, the fermentation tank converts sugar, starch, or cellulose to alcohol with the yeast cells, and the alcohol is separated with distillation.

In some embodiments, the feedstock is selected from the group consisting of: corn, wheat, barley, potatoes, switchgrass, *Miscanthus*, poplar wood, rice straw, corn stover, wheat straw, sugarcane bagasse, rice hulls, corn fiber, sugar beet pulp, citrus pulp, citrus peels, hardwood, softwood thinnings, hardwood and softwood residues from timber operations, wood shavings, sawdust, paper fraction of municipal solid waste, municipal wood waste, municipal green waste, saw mill waste, pulp mill waste, construction waste, demolition waste, wood shavings, sawdust, waste paper, materials containing sugar, starch, and cellulose.

In some embodiments, the variant polypeptide hydrolyzes phytate to inositol and free phosphate with release of minerals from the phytic acid. In some embodiments, the phytic acid is phytate in the form of calcium salts, magnesium salts, metal ions, proteins, unhydrolyzed phytate sludge, or myo-inositol-hexaphosphate.

In some embodiments, the variant polypeptide is used in combination with one or more other enzymes. In some embodiments, the one or more other enzymes comprise an amylase, a glucoamylase, a glucanase, a cellulase, an endoglucanase, a mannase, a xylanase, a xanthanase, a glycosidases, a cellobiohydrolase, a beta-glucosidase, a pullanase, a glucoisomerase, an alpha-glucosidase, or a combination thereof. In some embodiments, the variant polypeptide retains phytase activity under conditions from pH 2.5 to pH 12.0.

BRIEF DESCRIPTION OF THE DRAWINGS

FIGS. 2*a*, 2*b*, and 2*c* graphically summarizes yeast health data including yeast cell count and yeast viability.

FIGS. 3*a*, 3*b*, and 3*c* graphically summarizes data on ethanol yield, glycerol levels, and total sugar levels.

DETAILED DESCRIPTION

Definitions

Figure 1:
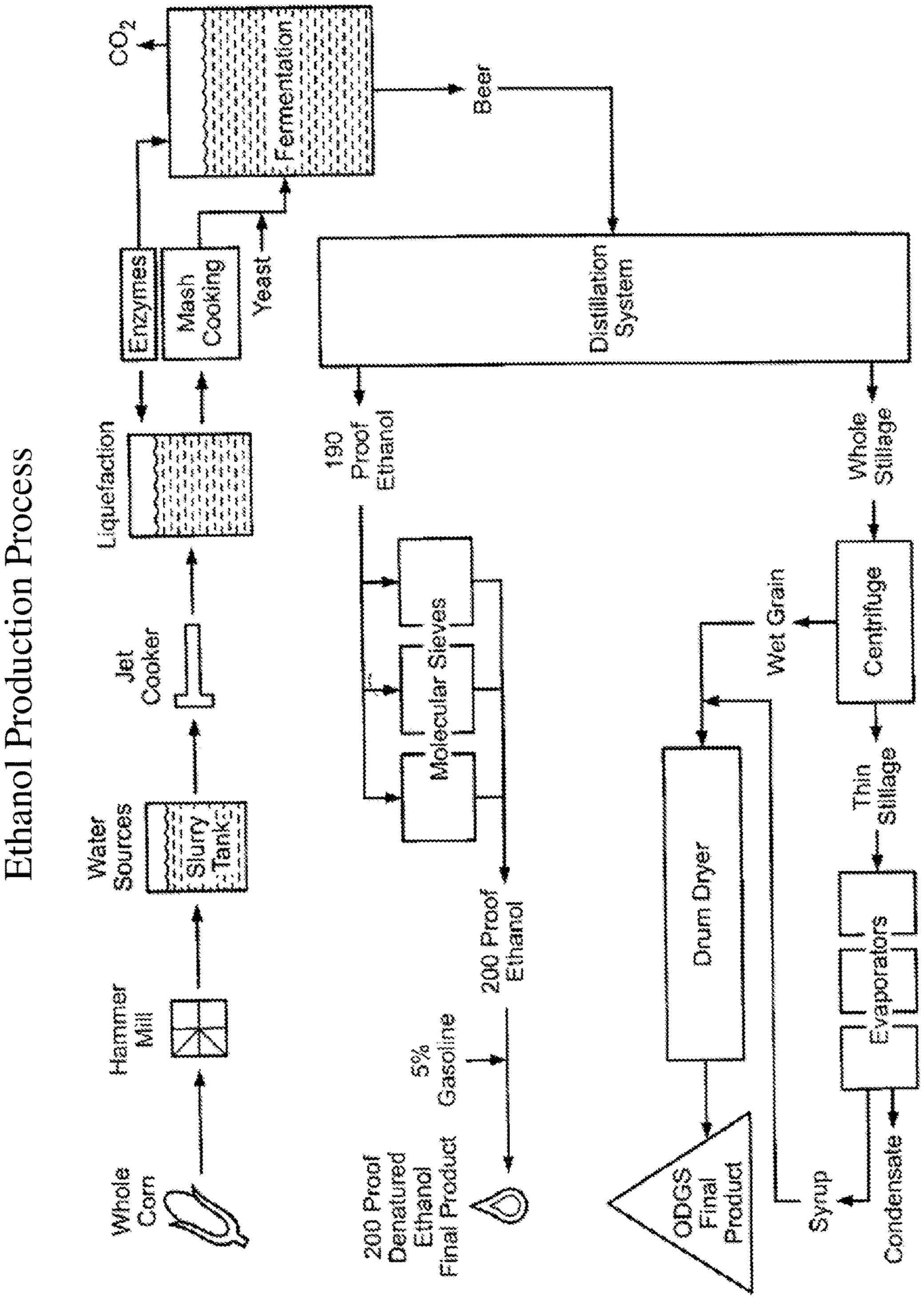
FIG. 1 illustrates an exemplary alcohol process that can incorporate the use of phytases disclosed herein.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the singular forms “a”, “an”, and “the” include plural references unless indicated otherwise, expressly or by context. For example, “a” dimer includes one or more dimers, unless indicated otherwise, expressly or by context.

As used herein, the terms “polynucleotide,” “oligonucleotide,” “nucleic acid” and “nucleic acid molecule” are used interchangeably to refer to a polymeric form of nucleotides of any length, and can comprise ribonucleotides, deoxyribonucleotides, analogs thereof, or mixtures thereof. This term refers only to the primary structure of the molecule. Thus, the term includes triple-, double- and single-stranded deoxyribonucleic acid (“DNA”), as well as triple-, double- and single-stranded ribonucleic acid (“RNA”). It also includes modified, for example by alkylation, and/or by capping, and unmodified forms of the polynucleotide. More particularly, the terms “polynucleotide,” “oligonucleotide,” “nucleic acid” and “nucleic acid molecule” include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glyco side of a purine or pyrimidine base, and other polymers containing nucleotidic backbones, for example, polyamide (e.g., peptide nucleic acids (“PNAs”)) and polymorpholino (commercially available from the Anti-Virals, Inc., Corvallis, OR., as NeuGene®) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, “caps,” substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g., nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

As used herein, polypeptides refer to lengthy, linear chains of amino acid monomers bound together by peptide bonds. A “purified” or “isolated” polypeptide or a “substantially pure” preparation of a polypeptide are used interchangeably herein and, as used herein, mean a polypeptide that has been separated from other proteins, carbohydrates, lipids, nucleic acids, and other biological materials with which it is naturally associated. Preferably, the polypeptide is also separated from substances, e.g., antibodies or gel matrix, e.g., polyacrylamide, which are used to purify it. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Fragments of the variant polypeptides of the present invention can retain at least one phytase-specific activity or epitope. Phytase activity can be assayed by examining the catalysis of phytate to inositol and free phosphate. For example, a phytase polypeptide fragment containing, e.g., at least 8-10 amino acids can be used as an immunogen in the production of phytase-specific antibodies. The fragment can contain, for example, an amino acid sequence that is conserved in phytases, and this amino acid sequence can contain amino acids that are conserved in phytases. Such fragments can easily be identified by comparing the sequences of phytases. The length of comparison in determining amino acid sequence homology can be, for example, at least 15 amino acids, for example, at least 20, 25, or 35 amino acids. Homology can be measured using standard sequence analysis software.

As used herein, “sequence identity” or “identity” or “homology” in the context of two protein or polypeptide sequences (or nucleotide sequences) includes reference to the residues in the two sequences which are the same when aligned for maximum correspondence over a specified comparison window. The portion of the amino acid sequence or nucleotide sequence in the comparison window can comprise additions or deletions (i.e., gaps) as compared to the reference sequence for optimal alignment of the two sequences. When percentage of sequence identity is used in reference to proteins it is recognized that residue positions which are not identical often differ by conservative amino acid substitutions, where amino acids are substituted for other amino acid residues with similar chemical properties (e.g. charge or hydrophobicity) and therefore do not change the functional properties of the molecule. Where sequences differ in conservative substitutions, the percentage sequence identity can be adjusted upwards to correct for the conservative nature of the substitutions. Sequences, which differ by such conservative substitutions are said to have "sequence similarity" or "similarity". Means for making these adjustments are well known to persons skilled in the art. The percentage is calculated by determining the number of positions at which the identical amino acid or nucleic acid base residue occurs in both sequences to yield the number of matched positions, dividing the number of matched positions by the total number of positions in the window of comparison and multiplying the result by 100 to yield the percentage of sequence identity. Typically this involves scoring a conservative substitution as a partial rather than a full mismatch, thereby increasing the percentage sequence identity. Thus, for example, where an identical amino acid is given a score of 1 and a non-conservative substitution is give a score of zero, a conservative substitution is given a score between 0 and 1. The scoring of conservative substitutions is calculated, e.g. according to the algorithm of Meyers and Miller (*Computer Applic. Biol. Sci.,* 1998, 4, 11-17).

As used herein, "substantially complementary" or "substantially matched" means that two nucleic acid sequences have at least about 70% sequence identity. Preferably, the two nucleic acid sequences have at least about 70%, 80%, 85%, 90%, 95%, 96%, 97%, 98%, 99% or 100% of sequence identity. Alternatively, "substantially complementary" or "substantially matched" means that two nucleic acid sequences can hybridize under high stringency condition(s).

As used herein, "carbohydrates," "saccharide" or "sugar" refer to a macromolecule consisting of carbon (C), hydrogen (H), and oxygen (O) atoms, usually with a hydrogen:oxygen atom ratio of 2:1 (as in water); in other words, with the empirical formula $C_m(H_2O)_n$ (where m could be different from n). Polysaccharides can have more than one saccharide and are used for the storage of energy. Monosaccharide and contain only one saccharide unit, while a disaccharide can contain two saccharide units, or two joined monosaccharides. As used herein, the term "total sugars" generally refers to combinations and varieties of non-ethanol sugars. However, the term may also be used to refer to any combination of sugars or saccharides.

As used herein, "enzyme" refers to a macromolecular catalyst. Enzymes are responsible for thousands of metabolic processes that sustain life. Enzymes are highly selective catalysts, greatly accelerating both the rate and specificity of metabolic reactions. Reactions can include but are not limited to the digestion of food, cleavage or breakdown of molecules, and the synthesis of DNA. Most enzymes are proteins, although some catalytic RNA molecules have been identified. Enzymes adopt a specific three-dimensional structure, and can employ organic (e.g. biotin) and inorganic (e.g. magnesium ion) cofactors to assist in catalysis. Enzymes are usually very specific as to which reactions they catalyze and the substrates that are involved in these reactions. Complementary shape, charge and hydrophilic/hydrophobic characteristics of enzymes and substrates are responsible for this specificity. Enzymes can also show high levels of specificity such as, stereospecificity, regioselectivity and chemoselectivity. By way of example and not of limitation, some enzymes can be used to break down large molecules such as, for example, starch, polyglycosides, sugars, proteins, branched sugars, liposaccharides, APG. In some embodiments, enzymes can be used to break down a micelle and release oil.

As used herein, "phytase" refers to any polypeptide, enzyme, or phosphatase that catalyzes the hydrolysis of phytates, phytic acids, myo-inositol hexaphosphates (or myo-inositol hexakisphosphates), inositol polyphosphate, inositol hexakisphosphates (IP6), or salts or compositions thereof into inorganic phosphorus, inorganic phosphates, and inositols.

As used herein, "cellulase" refers to an enzyme that can hydrolyze cellulose and polysaccharides to generate monosaccharides. In some embodiments, an enzyme comprising cellulase activity is provided.

As used herein, "glycoside hydrolase," "glycosidases" or "glycosyl hydrolases" are enzymes that can assist in the hydrolysis of glycosidic bonds in a complex sugar. The terms can be used interchangeably. These enzymes can degrade biomass such as, for example, cellulose, hemicellulose, APG, and glycosides. Glycosidases form the major catalytic machinery for the breakage of glycosidic bonds. In some embodiments, an enzyme comprising glycoside hydrolase activity is provided. In some embodiments, the enzyme can destabilize a micelle.

As used herein, "yeast cell count" refers to measurements of viable or non-viable yeast cells, separately or in any combination. Yeast cell counts may be measured using any method, including but not limited to the use of hemocytometers, counting chambers, microscope-based counting methods, electronic counting methods, automated counting techniques, or any manual or automated cell counting device or machinery (such as a Coulter counter). The term "living yeast cells" may also be used interchangeably with "viable yeast cells" and "dead yeast cells" interchangeably with "non-viable yeast cells" or "nonviable yeast cells". Calculations of yeast viability may be performed using any generally accepted method, including through 1) staining (e.g. methylene blue) to distinguish viable and non-viable yeast cells, 2) cell counting of viable and non-viable cells, and 3) calculating using the following formula: Yeast Viability %=[(Total counted cells−Total counted nonviable cells)/Total counted cells]×100.

Yeast budding percentages are often used for the calculation of yeast reproduction rates. A higher yeast reproduction rate may be directly correlated with an increased rate of ethanol or biofuel production. For this reason, optimization of yeast budding can be used to maximize production of ethanol production during the fermentation process. As used herein, budding yeast cells counts may be measured using any generally accepted method, including but not limited to the use of hemocytometers, counting chambers, microscope-based counting methods, electronic counting methods, automated counting techniques, or any manual or automated cell counting device or machinery (such as a Coulter counter). Yeast cell buds emerging from mother cells are counted as separate cells if the individual bud is at least one-half the size of the mother cell. These budding yeast cell counts may then be used in conjunction with viable or living yeast cell counts to determine the yeast budding percentage using the formula: Yeast Budding %=(Total budding cells/Total viable cells)×100.

As used herein, "fouling" refers to the accumulation of undesirable material on solid surfaces of devices, equipment, or machinery that inhibits their performance or function. Other commonly used terms may include deposition, deposition formation, scale formation, scaling, or scale deposition. "Fouling rate" refers to the rate at which such undesirable material accumulates. Higher fouling rate directly leads to decreased operation or online times for the ethanol production facility, increasing the cost of ethanol production.

As used herein, "online time" or "operation time" refers to the length of time that equipment or machinery may continuously function before cleaning, maintenance, or shutdown of the equipment or machinery becomes desirable or necessary. Equipment or machinery may be shut down due to a variety of reasons, but one particularly relevant cause in ethanol production is fouling. For example, once a sufficient amount of undesirable material has built up or deposited, the performance of some processing equipment will decrease until a cleaning process has been performed. The cleaning process may require acidic or caustic solutions, purified water, detergents, and the like. Lower online times increase both the time and financial costs of ethanol or biofuel production.

It is understood that aspects and embodiments of the disclosure described herein include "consisting" and/or "consisting essentially of" aspects and embodiments.

Other objects, advantages and features will become apparent from the following specification.

Polypeptides Having Phytase Activity

Some embodiments of the disclosure provide isolated, synthetic or recombinant nucleic acids comprising (a) (i) a nucleic acid sequence having at least 70%, 80%, 85%, 86%, 87%, 88%, 89%, 90%, 91%, 92%, 93%, 94%, 95%, 96% 97%, 98% or 99% sequence identity to SEQ ID NO:1, and comprising at least one, two, three, four, five, six, seven, eight, nine, ten, eleven, twelve, thirteen or fourteen nucleotide base pair sequence modifications to SEQ ID NO:1; (ii) a nucleic acid sequence having at least 70%, 80%, 85% 86%, 87%, 88%, 89%, 90%, 91%, 92%, 93%, 94%, 95%, 96% 97%, 98%, or 99% sequence identity to SEQ ID NO:1, and comprising at least one, two, three, four, five, six, seven, eight, nine, ten, eleven, twelve, thirteen or fourteen nucleotide base pair sequence modifications to SEQ ID NO:1; (iii) a polynucleotide encoding a polypeptide having a sequence comprising at least one, two, three, four, five, six, seven, eight, nine, ten, eleven, twelve, thirteen or fourteen amino acid residue modifications to SEQ ID NO: 2; or (iv) a polynucleotide encoding a polypeptide having a sequence comprising at least 70%, 80%, 85% 86%, 87%, 88%, 89%, 90%, 91%, 92%, 93%, 94%, 95%, 96% 97%, 98%, or 99% sequence identity to SEQ ID NO: 2, wherein the nucleic acids encode at least one polypeptide having a phytase activity and optionally the sequence identities are determined by analysis with a sequence comparison algorithm or by a visual inspection; or, (b) sequences fully complementary thereof.

Some embodiments of the disclosure provide (i) a polynucleotide encoding a polypeptide having a sequence comprising at least one, two, three, four, five, six, seven, eight, nine, ten, eleven, twelve, thirteen or fourteen amino acid residue modifications to SEQ ID NO: 3; or (ii) a polynucleotide encoding a polypeptide having a sequence comprising at least 70%, 80%, 85% 86%, 87%, 88%, 89%, 90%, 91%, 92%, 93%, 94%, 95%, 96% 97%, 98%, or 99% sequence identity to SEQ ID NO: 3, wherein the nucleic acids encode at least one polypeptide having a phytase activity and optionally the sequence identities are determined by analysis with a sequence comparison algorithm or by a visual inspection; or, (b) sequences fully complementary thereof.

Some embodiments of the disclosure provide a polypeptide having a sequence comprising at least one, two, three, four, five, six, seven, eight, nine, ten, eleven, twelve, thirteen or fourteen amino acid residue modifications to amino acid residues 23-434 of SEQ ID NO: 2; or (v) a polypeptide having a sequence comprising at least 70%, 80%, 85% 86%, 87%, 88%, 89%, 90%, 91%, 92%, 93%, 94%, 95%, 96% 97%, 98%, or 99% sequence identity to amino acid residues 23-434 of SEQ ID NO: 2.

Some embodiments of the disclosure provide a polypeptide having a sequence comprising at least one, two, three, four, five, six, seven, eight, nine, ten, eleven, twelve, thirteen or fourteen amino acid residue modifications to SEQ ID NO: 2; or (v) a polypeptide having a sequence comprising at least 70%, 80%, 85% 86%, 87%, 88%, 89%, 90%, 91%, 92%, 93%, 94%, 95%, 96% 97%, 98%, or 99% sequence identity to SEQ ID NO: 2.

Some embodiments of the disclosure provide a polypeptide having a sequence comprising at least one, two, three, four, five, six, seven, eight, nine, ten, eleven, twelve, thirteen or fourteen amino acid residue modifications to SEQ ID NO: 3; or (v) a polypeptide having a sequence comprising at least 70%, 80%, 85% 86%, 87%, 88%, 89%, 90%, 91%, 92%, 93%, 94%, 95%, 96% 97%, 98%, or 99% sequence identity to SEQ ID NO: 3.

Some embodiments may provide a polynucleotide encoding a polypeptide having a sequence comprising at least 70%, 80%, 85% 86%, 87%, 88%, 89%, 90%, 91%, 92%, 93%, 94%, 95%, 96% 97%, 98%, or 99% sequence identity to a variant polypeptide as disclosed herein, wherein the nucleic acids encode at least one polypeptide having a phytase activity and optionally the sequence identities are determined by analysis with a sequence comparison algorithm or by a visual inspection; or, (b) sequences fully complementary thereof.

Some embodiments of the disclosure provide variant polypeptides with sequence homology to SEQ ID NO: 2 and having phytase activity. These variant polypeptides are labeled "PV-[number] and include:

PV001: A variant polypeptide comprising an amino acid sequence that is at least 85%, 86%, 87%, 88%, 89%, 90%, 91%, 92%, 93%, 94%, 95%, 96%, 97%, 98%, or 99% identical to the full length of the amino acid sequence as set forth in SEQ ID NO: 2; wherein the variant polypeptide has phytase activity.

PV002: A variant polypeptide comprising an amino acid sequence that is at least 85%, 86%, 87%, 88%, 89%, 90%, 91%, 92%, 93%, 94%, 95%, 96%, 97%, 98%, 99%, or 100% identical to the amino acid sequence as set forth in in amino acid residues 23-434 SEQ ID NO: 2; wherein the variant polypeptide has phytase activity.

PV003: A variant polypeptide comprising the full length amino acid sequence set forth in SEQ ID NO: 2 and one single amino acid substitution selected from the group consisting of: A47F, T48F, T48H, T48I, T48K, T48L, T48M, T48V, T48W, T48Y, L50W, M51A, M51G, M51L, G67A, W68E, Y79H, Y79N, Y79S, Y79W, Q84W, Q86H, A95P, K97C, K97E, K97V, P100A, P102A, P102Y, I107H, I107P, I108A, I108Q, I108R, I108S, I108Y, A109V, E113P, L126R, T136H, Q137F, Q137L, Q137V, Q137Y, D139Y, P145L, L146R, L146T, F147Y, N148K, N148M, N148R, P149L, P149N, 1150T1, 1150Y, K151H, K151P, C155Y, L157C, L157P, N159V, N159Q, N161K, V162L, V162T, T163R, T163P, D164R, L167S, S168E, G171M, G171S, S173G, S173H, S173V, I174F, G179R, R181Y, V191A, L192F, F194L, S197G, S208P, S211H, L216T, P217D, P217G, P217L, P217S, S218I, S218Y, N226C, A232P, V233W, Q275V, A236H, A236T, L244S, Q246W, Q247H, A248L, A248T, P254S, G257A, G257R, H263P, W265L, N266P, L269I, L269T, L269P, H272W, A274F, A274I, A274L, A274T, A274V, Q275V, Y277D, T282H, R289A, T291V, T291W, L296T, M298K, A299T Q309P, N339E, T341D, P343E, P343I, P343L, P343N, P343R, P343V, N348K, N348W, T349Y, G353C, L363P, Q377R, L379S, L379V, Q381S, S389H, S389V, G395E, G395I, G395L, G395Q, G395T, V422M, I427G, I427S, I427T, A429P, and any combination thereof, wherein said variant polypeptide has phytase activity.

PV004: A variant polypeptide comprising the full length amino sequences as set forth in SEQ ID NO: 2 and the combination of amino acid substitutions of M298K and A299T, wherein the variant polypeptide has phytase activity.

PV005: A variant polypeptide comprising the full length amino acid sequence set forth in SEQ ID NO: 2 and two amino acid substitution of M298K, A299T, and further comprising one single amino acid substitution selected from the group consisting of: A47F, T48F, T48H, T48I, T48K, T48L, T48M, T48V, T48W, T48Y, L50W, M51A, M51G, M51L, G67A, W68E, Y79H, Y79N, Y79S, Y79W, Q84W, Q86H, A95P, K97C, K97E, K97V, P100A, P102A, P102Y, I107H, I107P, I108A, I108Q, I108R, I108S, I108Y, A109V, E113P, L126R, T136H, Q137F, Q137L, Q137V, Q137Y, D139Y, P145L, L146R, L146T, F147Y, N148K, N148M, N148R, P149L, P149N, 1150T1, 1150Y, K151H, K151P, C155Y, L157C, L157P, N159V, N159Q, N161K, V162L, V162T, T163R, T163P, D164R, L167S, S168E, G171M, G171S, S173G, S173H, S173V, I174F, G179R, R181Y, V191A, L192F, F194L, S197G, S208P, S211H, L216T, P217D, P217G, P217L, P217S, S218I, S218Y, N226C, A232P, V233W, Q275V, A236H, A236T, L244S, Q246W, Q247H, A248L, A248T, P254S, G257A, G257R, H263P, W265L, N266P, L269I, L269T, L269P, H272W, A274F, A274I, A274L, A274T, A274V, Q275V, Y277D, T282H, R289A, T291V, T291W, L296T, M298K, A299T Q309P, N339E, T341D, P343E, P343I, P343L, P343N, P343R, P343V, N348K, N348W, T349Y, G353C, L363P, Q377R, L379S, L379V, Q381S, S389H, S389V, G395E, G395I, G395L, G395Q, G395T, V422M, I427G, I427S, I427T, A429P, wherein said variant polypeptide has phytase activity.

PV006: A variant polypeptide comprising the full length amino sequences as set forth in SEQ ID NO: 2 and the combination of amino acid substitutions of W68E, M298K and A299T, wherein said variant polypeptide has phytase activity.

PV007: A variant polypeptide comprising the full length amino sequences as set forth in SEQ ID NO: 2 and the combination of amino acid substitutions of Q84W, M298K and A299T, wherein said variant polypeptide has phytase activity.

PV008: A variant polypeptide comprising the full length amino sequences as set forth in SEQ ID NO: 2 and the combination of amino acid substitutions of A95P, M298K and A299T, wherein said variant polypeptide has phytase activity.

PV009: A variant polypeptide comprising the full length amino sequences as set forth in SEQ ID NO: 2 and the combination of amino acid substitutions of K97C, M298K and A299T, wherein said variant polypeptide has phytase activity.

PV010: A variant polypeptide comprising the full length amino sequences as set forth in SEQ ID NO: 2 and the combination of amino acid substitutions of S168E, M298K and A299T, wherein said variant polypeptide has phytase activity.

PV011: A variant polypeptide comprising the full length amino sequences as set forth in SEQ ID NO: 2 and the combination of amino acid substitutions of R181Y, M298K and A299T, wherein said variant polypeptide has phytase activity.

PV012: A variant polypeptide comprising the full length amino sequences as set forth in SEQ ID NO: 2 and the combination of amino acid substitutions of N226, M298K and A299T, wherein said variant polypeptide has phytase activity.

PV013: A variant polypeptide comprising the full length amino sequences as set forth in SEQ ID NO: 2 and the combination of amino acid substitutions of Y277D, M298K and A299T, wherein said variant polypeptide has phytase activity.

PV014: A variant polypeptide comprising the full length amino sequences as set forth in SEQ ID NO: 2 and the combination of amino acid substitutions of Q84W, A95P, M298K and A299T, wherein said variant polypeptide has phytase activity.

PV015: A variant polypeptide comprising the full length amino sequences as set forth in SEQ ID NO: 2 and the combination of amino acid substitutions of Q84W, A95P, Y277D, M298K and A299T, wherein said variant polypeptide has phytase activity.

PV016: A variant polypeptide comprising the full length amino sequences as set forth in SEQ ID NO: 2 and the combination of amino acid substitutions of W68E, Q84W, A95P, Y277D, M298K and A299T, wherein said variant polypeptide has phytase activity.

PV017: A variant polypeptide comprising the full length amino sequences as set forth in SEQ ID NO: 2 and the combination of amino acid substitutions of W68E, Q84W, K97C, Y277D, M298K and A299T, wherein said variant polypeptide has phytase activity.

PV018: A variant polypeptide comprising the full length amino sequences as set forth in SEQ ID NO: 2 and the combination of amino acid substitutions of W68E, Q84W, K97C, R181Y, Y277D, M298K and A299T, wherein said variant polypeptide has phytase activity.

PV019: A variant polypeptide comprising the full length amino sequences as set forth in SEQ ID NO: 2 and the combination of amino acid substitutions of W68E, Q84W, A95P, K97C, R181Y, Y277D, M298K and A299T, wherein said variant polypeptide has phytase activity.

PV020: A variant polypeptide comprising the full length amino sequences as set forth in SEQ ID NO: 2 and the combination of amino acid substitutions of W68E, Q84W, A95P, K97C, R181Y, N226C, Y277D, M298K and A299T, wherein said variant polypeptide has phytase activity.

PV021: A variant polypeptide comprising the full length amino sequences as set forth in SEQ ID NO: 2 and the combination of amino acid substitutions of W68E, Q84W, A95P, K97C, S168E, R181Y, N226C, Y277D, M298K and A299T, wherein said variant polypeptide has phytase activity.

PV022: A variant polypeptide comprising the full length amino sequences as set forth in SEQ ID NO: 2 and the combination of amino acid substitutions of A47F, W68E, Q84W, A95P, K97C, S168E, R181Y, N226C, Y277D, M298K and A299T, wherein said variant polypeptide has phytase activity.

PV023: A variant polypeptide comprising the full length amino sequences as set forth in SEQ ID NO: 2 and the combination of amino acid substitutions of W68E, Q84W, A95P, K97E, S168E, R181Y, N226C, Y277D, M298K and A299T, wherein said variant polypeptide has phytase activity.

PV024: A variant polypeptide comprising the full length amino sequences as set forth in SEQ ID NO: 2 and the combination of amino acid substitutions of W68E, Q84W, A95P, K97V, S168E, R181Y, N226C, Y277D, M298K and A299T, wherein said variant polypeptide has phytase activity.

PV025: A variant polypeptide comprising the full length amino sequences as set forth in SEQ ID NO: 2 and the combination of amino acid substitutions of W68E, Q84W, A95P, K97C, T136H, S168E, R181Y, N226C, Y277D, M298K and A299T, wherein said variant polypeptide has phytase activity.

PV026: A variant polypeptide comprising the full length amino sequences as set forth in SEQ ID NO: 2 and the combination of amino acid substitutions of W68E, Q84W, A95P, K97C, N159V, S168E, R181Y, N226C, Y277D, M298K and A299T, wherein said variant polypeptide has phytase activity.

PV027: A variant polypeptide comprising the full length amino sequences as set forth in SEQ ID NO: 2 and the combination of amino acid substitutions of W68E, Q84W, A95P, K97C, N159E, S168E, R181Y, N226C, Y277D, M298K and A299T, wherein said variant polypeptide has phytase activity.

PV028: A variant polypeptide comprising the full length amino sequences as set forth in SEQ ID NO: 2 and the combination of amino acid substitutions of W68E, Q84W, A95P, K97C, T163R, S168E, R181Y, N226C, Y277D, M298K and A299T, wherein said variant polypeptide has phytase activity.

PV029: A variant polypeptide comprising the full length amino sequences as set forth in SEQ ID NO: 2 and the combination of amino acid substitutions of W68E, Q84W, A95P, K97C, D164R, S168E, R181Y, N226C, Y277D, M298K and A299T, wherein said variant polypeptide has phytase activity.

PV030: A variant polypeptide comprising the full length amino sequences as set forth in SEQ ID NO: 2 and the combination of amino acid substitutions of W68E, Q84W, A95P, K97C, S168R, R181Y, N226C, Y277D, M298K and A299T, wherein said variant polypeptide has phytase activity.

PV031: A variant polypeptide comprising the full length amino sequences as set forth in SEQ ID NO: 2 and the combination of amino acid substitutions of W68E, Q84W, A95P, K97C, S168E, G197R, R181Y, N226C, Y277D, M298K and A299T, wherein said variant polypeptide has phytase activity.

PV032: A variant polypeptide comprising the full length amino sequences as set forth in SEQ ID NO: 2 and the combination of amino acid substitutions of W68E, Q84W, A95P, K97C, S168E, R181Y, N226D, Y277D, M298K and A299T, wherein said variant polypeptide has phytase activity.

PV033: A variant polypeptide comprising the full length amino sequences as set forth in SEQ ID NO: 2 and the combination of amino acid substitutions of W68E, Q84W, A95P, K97C, S168E, R181Y, N226C, V233W, Y277D, M298K and A299T, wherein said variant polypeptide has phytase activity.

PV034: A variant polypeptide comprising the full length amino sequences as set forth in SEQ ID NO: 2 and the combination of amino acid substitutions of W68E, Q84W, A95P, K97C, S168E, R181Y, N226C, Q275V, Y277D, M298K and A299T, wherein said variant polypeptide has phytase activity.

PV035: A variant polypeptide comprising the full length amino sequences as set forth in SEQ ID NO: 2 and the combination of amino acid substitutions of W68E, Q84W, A95P, K97C, S168E, R181Y, N226C, Y277D, R289A, M298K and A299T, wherein said variant polypeptide has phytase activity.

PV036: A variant polypeptide comprising the full length amino sequences as set forth in SEQ ID NO: 2 and the combination of amino acid substitutions of W68E, Q84W, A95P, K97C, S168E, R181Y, N226C, Y277D, M298K, A299T and T349Y, wherein said variant polypeptide has phytase activity.

PV037: A variant polypeptide comprising the full length amino sequences as set forth in SEQ ID NO: 2 and the combination of amino acid substitutions of A47F, W68E, Q84W, A95P, K97E, T136H, N159V, S168E, G179R, R181Y, N226D, V233W, Q275V, Y277D, R289A, M298K, A299T and T349Y, wherein said variant polypeptide has phytase activity.

PV038: A variant polypeptide comprising the full length amino sequences as set forth in SEQ ID NO: 2 and the combination of amino acid substitutions of A47F, W68E, Q84W, A95P, K97E, N159V, T163R, D164R, S168E, G179R, R181Y, N226D, V233W, Q275, Y277D, M298K, T349Y, and A299T, wherein said variant polypeptide has phytase activity.

PV039: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, T163R, D164R, G179R, V233W, Q275V and T349Y, wherein said variant polypeptide has phytase activity.

PV040: A variant polypeptide comprising the full length amino sequences as set forth in SEQ ID NO: 2 and the combination of amino acid substitutions of W68E, Q84W, A95P, K97C, S168R, R181Y, N226D, Y277D, M298K, A299T, A47F, T136H, N159V, T163R, D164R, G179R, V233W, Q275V, R289A and T349Y, wherein said variant polypeptide has phytase activity.

PV041: A variant polypeptide comprising the full length amino sequences as set forth in SEQ ID NO: 2 and the combination of amino acid substitutions of W68E, Q84W, A95P, K97V, S168R, R181Y, N226D, Y277D, M298K, A299T, A47F, T136H, N159V, T163R, G179R, V233W, Q275V, R289A and T349Y, wherein said variant polypeptide has phytase activity.

PV042: A variant polypeptide comprising the full length amino sequences as set forth in SEQ ID NO: 2 and the combination of amino acid substitutions of W68E, Q84W, A95P, K97V, S168R, R181Y, N226D, Y277D, M298K, A299T, A47F, T136H, N159V, T163R, D164R, G179R, V233W, Q275V and T349Y, wherein said variant polypeptide has phytase activity.

PV043: A variant polypeptide comprising the full length amino sequences as set forth in SEQ ID NO: 2 and the combination of amino acid substitutions of W68E, Q84W, A95P, K97C, S168R, R181Y, N226D, Y277D, M298K, A299T, A47F, T136H, N159V, T163R, D164R, G179R, V233W, Q275V, and T349Y, wherein said variant polypeptide has phytase activity.

PV044: A variant polypeptide comprising the full length amino sequences as set forth in SEQ ID NO: 2 and the combination of amino acid substitutions of W68E, Q84W, A95P, K97E, S168E, R181Y, N226D, Y277D, M298K, A299T, A47F, T136H, N159V, T163R, D164R, G179R, V233W, Q275V, and T349Y, wherein said variant polypeptide has phytase activity.

PV045: A variant polypeptide comprising the full length amino sequences as set forth in SEQ ID NO: 2 and the combination of amino acid substitutions of W68E, Q84W, A95P, K97E, S168R, R181Y, N226C, Y277D, M298K, A299T, A47F, T136H, N159V, T163R, D164R, G179R, V233W, Q275V, R289A, and T349Y, wherein said variant polypeptide has phytase activity.

PV046: A variant polypeptide comprising the full length amino sequences as set forth in SEQ ID NO: 2 and the combination of amino acid substitutions of W68E, Q84W, A95P, K97E, S168E, R181Y, N226C, Y277D, M298K, A299T, A47F, T136H, N159E, T163R, D164R, G179R, V233W, Q275V, R289A, T349Y, and L363P, wherein said variant polypeptide has phytase activity.

PV047: A variant polypeptide comprising the full length amino sequences as set forth in SEQ ID NO: 2 and the combination of amino acid substitutions of W68E, Q84W, A95P, K97V, S168E, R181Y, N226C, Y277D, M298K, A299T, A47F, T136H, N159V, T163R, D164R, G179R, V233W, Q275V, R289A, and T349Y, wherein said variant polypeptide has phytase activity.

PV048: A variant polypeptide comprising the full length amino sequences as set forth in SEQ ID NO: 2 and the combination of amino acid substitutions of W68E, Q84W, A95P, K97E, S168R, R181Y, N226D, Y277D, M298K, A299T, A47F, T136H, N159V, T163R, D164R, G179R, V233W, Q275V, R289A and T349Y, wherein said variant polypeptide has phytase activity.

PV049: A variant polypeptide comprising the full length amino sequences as set forth in SEQ ID NO: 2 and the combination of amino acid substitutions of W68E, Q84W, A95P, K97E, S168E, R181Y, N226D, Y277D, M298K, A299T, A47F, N159V, D164R, G179R, V233W, Q275V, R289A, and T349Y, wherein said variant polypeptide has phytase activity.

PV050: A variant polypeptide comprising the full length amino sequences as set forth in SEQ ID NO: 2 and the combination of amino acid substitutions of W68E, Q84W, A95P, K97E, S168R, R181Y, N226D, Y277D, M298K, A299T, A47F, N159V, T163R, D164R, G179R, V233W, Q275V, R289A, and T349Y, wherein said variant polypeptide has phytase activity.

PV051: A variant polypeptide comprising the full length amino sequences as set forth in SEQ ID NO: 2 and the combination of amino acid substitutions of W68E, Q84W, A95P, K97V, S168R, R181Y, N226D, Y277D, M298K, A299T, A47F, T136H, N159E, T163R, D164R, G179R, V233W, Q275V, R289A, and T349Y, wherein said variant polypeptide has phytase activity.

PV052: A variant polypeptide comprising the full length amino sequences as set forth in SEQ ID NO: 2 and the combination of amino acid substitutions of W68E, Q84W, A95P, K97E, S168E, R181Y, N226D, Y277D, M298K, A299T, A47F, T136H, N159V, T163R, G179R, V233W, Q275V, and T349Y, wherein said variant polypeptide has phytase activity.

PV053: A variant polypeptide comprising the full length amino sequences as set forth in SEQ ID NO: 2 and the combination of amino acid substitutions of W68E, Q84W, A95P, K97E, S168R, R181Y, N226D, Y277D, M298K, A299T, A47F, C97E, T136H, N159V, T163R, D164R, G179R, V233W, Q275V, and T349Y, wherein said variant polypeptide has phytase activity.

PV054: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159E, T163R, D164R, G179R, V233W, Q275V, R289A, and T349Y, wherein said variant polypeptide has phytase activity.

PV055: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, V233W, Q275V, and T349Y, wherein said variant polypeptide has phytase activity.

PV056: A variant polypeptide comprising the full length amino sequences as set forth in SEQ ID NO: 2 and the combination of amino acid substitutions of W68E, Q84W, A95P, K97V, S168E, R181Y, N226D, Y277D, M298K, A299T, A47F, T136H, N159V, D164R, G179R, V233W, Q275V and T349Y, wherein said variant polypeptide has phytase activity.

PV057: A variant polypeptide comprising the full length amino sequences as set forth in SEQ ID NO: 2 and the combination of amino acid substitutions of W68E, Q84W, A95P, K97V, S168E, R181Y, N226C, Y277D, M298K, A299T, A47F, T136H, N159V, D164R, G179R, V233W, Q275V, and T349Y, wherein said variant polypeptide has phytase activity.

PV058: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, V233W, and T349Y, wherein said variant polypeptide has phytase activity.

PV059: A variant polypeptide comprising the full length amino sequences as set forth in SEQ ID NO: 2 and the combination of amino acid substitutions of W68E, Q84W, A95P, K97E, T136H, N159V, T163R, D164R, S168R, G179R, R181Y, N226D, Q275V, Y277D, M298K, A299T, and T349Y, wherein said variant polypeptide has phytase activity.

PV060: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, C226D, V233W, T291V, and T349Y; wherein said variant polypeptide has phytase activity.

PV061: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, V233W, A236T, and T349Y; wherein said variant polypeptide has phytase activity.

PV062: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, L157 P, N159V, V233W, and T349Y; wherein said variant polypeptide has phytase activity.

PV063: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, L157P, N159V, D164R, G179R, V233W, Q275V, and T349Y; wherein said variant polypeptide has phytase activity.

PV064: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, V233W, S236T Q275V, and T349Y; wherein said variant polypeptide has phytase activity.

PV065: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, V233W, Q275V, T291V, and T349Y; wherein said variant polypeptide has phytase activity.

PV066: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, L192F, V233W, and T349Y; wherein said variant polypeptide has phytase activity.

PV067: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, L192F, V233W, T291V, and T349Y; wherein said variant polypeptide has phytase activity.

PV068: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, L192F, V233W, Q275V, and T349Y; wherein said variant polypeptide has phytase activity.

PV069: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, V233W, Q275V, T291V, and T349Y; wherein said variant polypeptide has phytase activity.

PV070: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, L192F, V233W, Q275V, T291V, and T349Y; wherein said variant polypeptide has phytase activity.

PV071: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, L192F, V233W, A236T, and T349Y; wherein said variant polypeptide has phytase activity.

PV072: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, V233W, A236T, T291V, and T349Y; wherein said variant polypeptide has phytase activity.

PV073: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, L192F, V233W, A236T, T291V, and T349Y; wherein said variant polypeptide has phytase activity.

PV074: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, L192F, V233W, A236T, Q275V, and T349Y; wherein said variant polypeptide has phytase activity.

PV075: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, V233W, A236T, Q275V, T291V, and T349Y; wherein said variant polypeptide has phytase activity.

PV076: A variant polypeptide comprising the full length amino sequences as set forth in SEQ ID NO: 2 and the combination of amino acid substitutions of W68E, Q84W, A95P, K97C, S168E, R181Y, N226D, Y277D, M298K, A299T, A47F, T136H, N159V, D164R, G179R, L192F, V233W, A236T, Q275V, T291V, and T349Y; wherein said variant polypeptide has phytase activity.

PV077: Any of the variant polypeptides as described above, wherein the amino acid sequence is set forth in amino acid residues 23-440 SEQ ID NO: 2, and said variant polypeptide has phytase activity.

PV078: Any of the variant polypeptides as described above, wherein the amino acid sequence is set forth in amino acid residues 1-434 SEQ ID NO: 2, and said variant polypeptide has phytase activity.

PV079: Any of the variant polypeptides described above, wherein the amino acid sequence is set forth in amino acid residues 23-434 SEQ ID NO: 2, and said variant polypeptide has phytase activity.

Some embodiments of the disclosure provide variant polypeptides having phytase activity with sequence homology to SEQ ID NO: 3. The variant polypeptides with phytase activity and sequence homology to SEQ ID NO: 3 are labeled "PhV-[number]" and include at least the described modifications. These variant polypeptides comprise the full length amino sequences as set forth in SEQ ID NO: 3 and the combination of amino acid substitutions following:

PhV-001 D2E A4E A6S F8Y N33M K76N N78T D92N Q121T A123V T152G S164E A200N D258N S261H N270Q H374N D398E

PhV-002 D2E A4E A6S F8Y N33M K76N N78T D92A Q121T A123V T152G S164E A200N D258N S261H N270Q H374N D398E

PhV-003 D2E A4E A6S F8Y N33M R67L K76N N78T D92A Q121T A123V T152G S164E A200N D258N M260I S261H N270Q H374N D398E

PhV-004 D2E A4E A6S F8Y N33M R67L K76N N78T D92N Q109N Q121T A123V A144E T152G Q159N S164E A200N S217G D258N M260I S261H N270Q H374N D398E

PhV-020 S1-D2-T3Q A4G P5A A6D G7K F8M Q9K K12R N33M K76N N78T D92N Q121T T152G S164E A200N D258N S261H N270Q H374N

PhV-031 D2E A4E A6S F8Y N33M K76N N78T D92N Q121T S164E A200N D258N S261H N270Q H374N

PhV-048 S1-D2-T3Q A4G P5A A6D G7K F8M Q9K K12R N33M K76I N78T D92N Q121T T152G S164E A200N D258N S261H N270Q H374N

PhV-053 S1-D2-T3Q A4G P5A A6D G7K F8M Q9K K12R N33M K76N N78T D92N Q121T A123V T152G S164E A200N D258N S261H N270Q I300L H374N

PhV-055 D2E A4E A6S F8Y N33M K76N N78T D92N Q121T T152G S164E A200N D258N S261H N270Q Q276N H374N

PhV-058 D2E A4E A6S F8Y N33M K76N N78T D92N Q121T T152G S164E A200N D258N S261H N270Q H374N

PhV-059 D2E A4E A6S F8Y N33M K76N N78T D92N Q121T T152G S164E A200N D258N S261H N270Q H374N D398E

PhV-060 S1-D2-T3Q A4G P5A A6D G7K F8M Q9K K12R N33M K76N N78T D92N Q109N Q121T T152G S164E A200N D258N S261H N270Q I300L N346G H374N

PhV-064 S1-D2-T3Q A4G P5A A6D G7K F8M Q9K K12R K76N N78T D92A Q121T S164E A200N D258N S261H N270Q H374N

PhV-065 S1-D2-T3Q A4G P5A A6D G7K F8M Q9K K12R K76N N78T D92T Q121T S164E A200N D258N S261H N270Q H374N

PhV-066 S1-D2-T3Q A4G P5A A6D G7K F8M Q9K K12R K76N N78T D92V Q121T S164E A200N D258N S261H N270Q H374N

PhV-067 S1-D2-T3Q A4G P5A A6D G7K F8M Q9K K12R K76N N78T D92A Q121T A123V S164E A200N D258N S261H N270Q H374N

PhV-068 S1-D2-T3Q A4G P5A A6D G7K F8M Q9K K12R K76N N78T D92E Q121T A123V S164E A200N D258N S261H N270Q H374N

PhV-069 S1-D2-T3Q A4G P5A A6D G7K F8M Q9K K12R K76N N78T D92T Q121T A123V S164E A200N D258N S261H N270Q H374N

PhV-070 S1-D2-T3Q A4G P5A A6D G7K F8M Q9K K12R K76N N78T D92V Q121T A123V S164E A200N D258N S261H N270Q H374N

PhV-072 S1-D2-T3Q A4G P5A A6D G7K F8M Q9K K12R K76N N78T D92E Q121T S164E A200N D258N S261H N270Q H374N

PhV-073 S1-D2-T3Q A4G P5A A6D G7K F8M Q9K K12R K76I N78T D92N Q109N Q121T S164E A200N D258N S261H N270Q I300L H374N

PhV-074 S1-D2-T3Q A4G P5A A6D G7K F8M Q9K K12R K76I N78T D92N Q109N Q121T S164E A200N D258N S261H N270Q I300L H374N D398E

PhV-075 S1-D2-T3Q A4G P5A A6D G7K F8M Q9K K12R K76N N78T D92N Q109N Q121T A144E S164E A200N S217G D258N S261H N270Q I300L H374N

PhV-076 S1-D2-T3Q A4G P5A A6D G7K F8M Q9K K12R K76N N78T D92A Q121T A123V S164E A200N D258N S261H N270Q I300L H374N

PhV-077 S1-D2-T3Q A4G P5A A6D G7K F8M Q9K K12R K76N N78T D92E Q121T A123V S164E A200N D258N S261H N270Q I300L H374N

PhV-078 S1-D2-T3Q A4G P5A A6D G7K F8M Q9K K12R K76N N78T D92T Q121T A123V S164E A200N D258N S261H N270Q I300L H374N

PhV-079 S1-D2-T3Q A4G P5A A6D G7K F8M Q9K K12R K76N N78T D92V Q121T A123V S164E A200N D258N S261H N270Q I300L H374N

PhV-081 D2E A4E A6S F8Y N33M K76N N78T D92N Q121T A123V T152G S164E A200N D258N S261H N270Q H374N D398E

PhV-083 D2E A4E A6S F8Y N33M K76N N78T D92N Q121T T152G S164E A200N D258N S261H N270Q Q276N I300L H374N D398E

PhV-084 S1-D2-T3Q A4G P5A A6D G7K F8M Q9K K12R K76N N78T D92A Q121T S136K S164E A200N D258N S261H N270Q H374N

PhV-085 S1-D2-T3Q A4G P5A A6D G7K F8M Q9K K12R K76I N78T D92A Q109N Q121T S164E A200N D258N S261H N270Q I300L H374N

PhV-088 D2E A4E A6S F8Y N33M K76N N78T D92N Q121T T152G T156G S164E A200N D258N S261H N270Q H374N D398E

PhV-089 D2E A4E A6S F8Y N33M K76N N78T D92N Q121T T152G S164E A200N D258N S261H N270Q I300L H374N D398E

PhV-094 S1-D2-T3Q A4G P5A A6D G7K F8M Q9K K12R N33M K76N N78T D92N Q109N Q121T A123V T152G T156G S164E A200N D258N S261H N270Q Q276N I300L N346G H374N

PhV-095 S1-D2-T3Q A4G P5A A6D G7K F8M Q9K K12R N33M K76I N78T D92N Q121T A144E T152G S164E A200N S217G D258N S261H N270Q H374N D398E

PhV-096 S1-D2-T3Q A4G P5A A6D G7K F8M Q9K K12R K76I N78T D92A Q121T A123V S164E A200N D258N S261H N270Q H374N

PhV-097 S1-D2-T3Q A4G P5A A6D G7K F8M Q9K K12R K76N N78T D92A Q109N Q121T A123V Q159N S164E A200N D258N S261H N270Q H374N

PhV-098 S1-D2-T3Q A4G P5A A6D G7K F8M Q9K K12R K76N N78T D92A Q121T S136K S164E A200N D258N S261H N270Q H374N

PhV-099 D2E A4E A6S F8Y N33D K76N N78T D92N Q121T T152G S164E A200N D258N S261H N270Q H374N

PhV-101 N33D K76N N78T D92N Q121T T152G S164E A200N H374N

PhV-103 N33D D92N Q121T T152G S164E A200N D258N S261H N270Q H374N

PhV-104 N33M K76N N78T D92N Q121T T152G S164E A200N D258N S261H N270Q H374N

PhV-105 N33D D92N S164E A200N D258N S261H N270Q H374N

PhV-106 N33D K76N N78T D92N Q121T T152G S164E A200N D258N S261H H374N

PhV-107 N33D K76N N78T D92N Q121T S164E A200N D258N S261H N270Q H374N

PhV-108 N33D D92N Q121T A123V A144E T152G S164E A200N S217G D258N S261H N270Q H374N

PhV-109 N33D D92N Q121T A123V A144E T152G Q159N S164E A200N D258N S261H N270Q H374N

PhV-110 N33D D92N Q121T T152G Q159N S164E A200N S217G D258N M260I S261H N270Q H374N

PhV-111 N33D D92A Q121T T152G Q159N S164E A200N S217G D258N M260I S261H N270Q H374N

PhV-112 S1-D2-T3Q A4G P5A N33D D92N Q121T T152G S164E A200N D258N S261H N270Q H374N

PhV-113 S1-D2-T3Q A4G P5A N33D D92N Q121T T152G S164E A200N D258N S261H N270Q H374N

PhV-114 A6D G7K F8M Q9K N33D D92N Q121T T152G S164E A200N D258N S261H N270Q H374N

PhV-115 N33D D92A Q121T A123V A144E T152G Q159N S164E A200N S217G D258N M260I S261H N270Q H374N

PhV-116 N33D D92N Q121T A123V A144E T152G Q159N S164E A200N S217G D258N M260I S261H N270Q H374N

PhV-117 S1A D2S T3R A4N N33D D92N Q121T T152G S164E A200N D258N S261H N270Q H374N

PhV-118 N33D D92N Q121T A123V A144E T152G S164E A200N S217G D258N M260I S261H N270Q H374N

PhV-119 N33D D92N Q121T T152G S164E A200N D258N S261H N270Q H374N

PhV-120 D2E A4E A6S F8Y N33M K76N N78T D92N Q121T T152G S164E A200N D258N S261H N270Q H374N

PhV-121 S1-D2-T3Q A4G P5A A6D G7K F8M Q9K K12R N33M K76N N78T D92N Q121T T152G S164E A200N D258N S261H N270Q H374N

PhV-122 N33M K76N N78T D92N Q121T T152G S164E A200N D258N S261H N270Q H374N

PhV-123 D2E A4E A6S F8Y N33D D92N S164E A200N H374N

PhV-124 D2E A4E A6S F8Y N33D K76N N78T D92N Q121T T152G S164E A200N D258N S261H H374N

PhV-125 N33D D92A Q121T A123V T152G S164E A200N D258N S261H N270Q H374N

PhV-126 N33D D92A Q121T A123V T152G S164E A200N D258N M260I S261H N270Q H374N

PhV-127 N33D D92N Q121T A144E T152G Q159N S164E A200N S217G D258N M260I S261H N270Q H374N

PhV-128 A4E A6S N33D D92N Q121T T152G S164E A200N D258N S261H N270Q H374N

PhV-129 N33D R67L D92N Q121T A144E T152G Q159N S164E A200N S217G D258N M260I S261H N270Q H374N

PhV-130 L16V N33D D92N Q121T A144E T152G Q159N S164E A200N S217G D258N M260I S261H N270Q H374N

PhV-131 K12R N33D D92N Q121T A144E T152G Q159N S164E A200N S217G D258N M260I S261H N270Q H374N

PhV-132 K12R L16V N33D D92N Q121T T152G Q159N S164E A200N S217G D258N M260I S261H N270Q H374N

PhV-133 N33D R67L D92N Q121T A123V T152G Q159N S164E A200N S217G D258N M260I S261H N270Q H374N

PhV-134 N33D D92N Q121T A144E T152G Q159N S164E A166E A200N S217G D258N M260I S261H N270Q H374N

PhV-135 N33D R67L D92N Q121T A123V A144E T152G Q159N S164E A166E A200N S217G D258N M260I S261H N270Q H374N

PhV-136 N33D D92A Q121T A123V A144E T152G Q159N S164E A166E A200N S217G D258N M260I S261H N270Q H374N

PhV-137 N33D D92A Q121T T152G Q159N S164E A166E A200N S217G D258N M260I S261H N270Q H374N D398E

PhV-138 N33D D92N Q121T A123V A144E T152G Q159N S164E A166E A200N S217G D258N M260I S261H N270Q H374N D398E

PhV-139 N33D D92N Q121T A144E T152G Q159N S164E A200N S217G D258N S261H N270Q H374N

PhV-140 K12R N33D R67L D92N Q121T A123V A144E T152G S164E A200N S217G D258N S261H N270Q H374N

PhV-141 L16V N33D R67L D92N Q121T A123V A144E T152G S164E A200N S217G D258N S261H N270Q H374N

PhV-142 N33D R67L D92N Q121T A123V A144E T152G S164E A166E A200N S217G D258N S261H N270Q H374N

PhV-143 N33D D92N Q121T A123V A144E T152G S164E A166E A200N S217G D258N S261H N270Q I300L H374N

PhV-144 N33D D92N I120L Q121T A123V A144E T152G S164E A200N S217G D258N S261H N270Q I300L H374N

PhV-145 N33D D92N I120L Q121T A123V A144E T152G S164E A200N S217G D258N S261H N270Q L371A H374N

PhV-146 N33D R67L D92N I120L Q121T A123V A144E T152G S164E A166E A200N S217G D258N S261H N270Q L371A H374N, or

PhV-147 N33D D92N I120L Q121T A123V A144E T152G S164E A200N S217G D258N S261H N270Q I300L L371A H374N.

Some embodiments of the disclosure provide methods for processing of phytates, phytic acids, or salts thereof are provided, comprising the following steps: (a) providing a polypeptide having a phytase activity, wherein the polypeptide comprises a polypeptide disclosed herein; (b) providing a composition comprising a phytate, phytic acid, or salts thereof; and (c) contacting the polypeptide of step (a) and the composition of step (b) under conditions wherein the polypeptide can cleave an inositol-inorganic phosphate linkage.

Some embodiments of the disclosure provide methods for hydrolyzing inositol-hexaphosphate compositions to inositol and inorganic phosphate comprising the following steps: (a) providing a polypeptide having a phytase activity, wherein the polypeptide comprises an amino acid sequence as disclosed herein, or, a polypeptide encoded by a nucleic acid sequence disclosed herein; (b) providing a composition comprising an inositol-hexaphosphate; and (c) contacting the polypeptide of step (a) with the composition of step (b) under conditions wherein the polypeptide hydrolyzes the inositol-hexaphosphate to produce to inositol and inorganic phosphate, and optionally the composition comprises a phytic acid. In some embodiments, the inositol-hexaphosphate compositions include phytate in the form of calcium salts, magnesium salts, metal ions, proteins, unhydrolyzed phytate sludge, or myo-inositol-hexaphosphate compositions.

In some embodiments, the phytase activity is thermotolerant, and optionally the polypeptide retains a phytase activity after exposure to a temperature in the range of between about 40° C. to about 70° C., or between about 37° C. to about 100° C., or from greater than 37° C. to about 50° C., 55° C., 60° C., 65° C., 70° C., 75° C., 80° C., 85° C., 90° C., 95° C., 100° C. or more. In some embodiments, the phytase activity is thermostable, and optionally the polypeptide retains a phytase activity at a temperature in the range of between about 40° C. to about 70° C., or between about 37° C. to about 100° C., or from greater than 37° C. to about 50° C., 55° C., 60° C., 65° C., 70° C., 75° C., 80° C., 85° C., 90° C., 95° C., 100° C. or more.

Some embodiments of the disclosure provide polypeptides that have phytase activity whose activity is thermotolerant, and optionally the polypeptide retains a phytase activity after exposure to a temperature in the range of from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermotolerant polypeptides can retain activity, e.g. a phytase activity, after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermotolerant polypeptides may retain activity, e.g. a phytase activity, after exposure to a temperature in the ranges described above, at about pH 2.0, about pH 2.5, about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

Some embodiments of the disclosure provide polypeptides that have phytase activity whose activity is thermostable. For example, a polypeptide as described herein can be thermostable. Optionally, the thermostable polypeptide can retain binding and/or enzymatic activity, e.g., a phytase activity, under conditions comprising a temperature range from about −100° C. to about −80° C., about −80° C. to about −40° C., about −40° C. to about −20° C., about −20° C. to about 0° C., about 0° C. to about 37° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermostable polypeptides can retain activity, e.g. a phytase activity, in temperatures in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermostable polypeptides may retain activity, e.g., a phytase activity, at a temperature in the ranges described above, at about pH 2.0, about pH 2.5, about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In some embodiments, the phytase activity of any polypeptide comprises a specific activity: at about 37° C. in the range from about 100 to about 1000 units per milligram of protein; or, from about 500 to about 750 units per milligram of protein; or, at 37° C. in the range from about 500 to about 1200 units per milligram of protein; or, at 37° C. in the range from about 750 to about 1000 units per milligram of protein. In some embodiments, the thermotolerant phytase activity comprises a specific activity after exposure to a temperature at about 37° C. in the range from about 100 to about 1000 units per milligram of protein; or, the thermostable phytase activity comprises a specific activity from about 500 to about 750 units per milligram of protein; or, the thermostable phytase activity comprises a specific activity at 37° C. in the range from about 500 to about 1200 units per milligram of protein; or, the thermostable phytase activity comprises a specific activity at 37° C. in the range from about 750 to about 1000 units per milligram of protein. In some embodiments, the thermostable phytase activity comprises a specific activity under conditions comprising a temperature of about 37° C. in the range from about 100 to about 1000 units per milligram of protein; or, the thermostable phytase activity comprises a specific activity from about 500 to about 750 units per milligram of protein; or, the thermostable phytase activity comprises a specific activity at 37° C. in the range from about 500 to about 1200 units per milligram of protein; or, the thermostable phytase activity comprises a specific activity at 37° C. in the range from about 750 to about 1000 units per milligram of protein.

In some embodiments, the polypeptide retains a phytase activity under conditions comprising about pH 6.5, pH 6, pH 5.5, pH 5, pH 4.5, pH 4.0, pH 3.5, pH 3.0 or less (more acidic) pH. In some embodiments, a polypeptide can retain a phytase activity under conditions comprising about pH 7.5, pH 8, pH 8.5, pH 9, pH 9.5, pH 10.0, pH 10.5, pH 11.0, pH 11.5, pH 12, pH 12.5 or more.

In some embodiments, the polypeptides disclosed herein may be a heterodimer, and in some embodiments the heterodimer comprises a second domain, wherein optionally the second domain is a polypeptide and the heterodimer is a fusion protein, and optionally the second domain is an epitope or a tag.

In some embodiments, immobilized polypeptides are provided, wherein the immobilized polypeptide comprises a homodimer or a heterodimer, wherein optionally the polypeptide is immobilized on or inside a cell, a vesicle, a liposome, a film, a membrane, a metal, a resin, a polymer, a ceramic, a glass, a microelectrode, a graphitic particle, a bead, a gel, a plate, an array, a capillary tube, a crystal, a tablet, a pill, a capsule, a powder, an agglomerate, a surface, or a porous structure. In some embodiments, provided herein are arrays (e.g., microarrays) comprising an immobilized polypeptide, wherein the polypeptide may be a heterodimer, or an immobilized nucleic acid, or a combination thereof.

In some embodiments, provided herein are pellets comprising a carrier and a polypeptide, or a homodimer or heterodimer thereof; wherein optionally the polypeptide is coated for controlled release, and optionally the phytase activity is thermotolerant or thermostable, and optionally the pellet is manufactured in pellet form, or as a pill, tablet, capsule, gel, geltab, spray, powder, lyophilized formulation, liquid form, film, as a suspension or slurry, or produced using polymer-coated additives, or manufactured in granulate form, or produced by spray drying.

In a broad sense, the variant polypeptides are isolated from, derived from, or recombined with gene products having any origin, including bacterium, fungi, animal, and plant origins. Examples of the origins may include, for example, *Bacillus, Aspergillus, Escherichia coli, Pseudomonas fluorescens, Pseudomonas sarccharophilla*, etc.

Methods for Improving Efficiency of Ethanol Production

Some embodiments disclosed herein provide methods for improving efficiency of ethanol production by yeast, the method comprising: (a) providing a variant polypeptide comprising an amino acid sequence that is at least 85% identical to the amino acid sequence as set forth in amino acid residues 23-434 of SEQ ID NO:2; wherein said variant polypeptide has phytase activity; and (b) adding the variant polypeptide to an ethanol processing fluid in an ethanol production facility, wherein addition of the variant polypeptide improves ethanol production efficiency compared to a wild-type phytase, a commercially available phytase, or no phytase. In some embodiments, the addition of the variant polypeptide at any step in the ethanol production process improves ethanol production efficiency compared to a production process where no phytase is added, a wild-type phytase is added, or a commercially available phytase is added. The improved efficiency in the ethanol production process comprises one or more of increased yeast cell count, yeast budding, or yeast viability, increased ethanol yield, decreased glycerol level or sugar level (e.g. total sugar levels). The improved efficiency in the ethanol production process comprises one or more of increased yeast cell count, yeast budding, or yeast viability, increased ethanol yield, glycerol level or sugar level; decreased fouling rate; increased phosphorous levels; and increased operation time of the ethanol production facility.

In some embodiments, the improved efficiency compared to a wild-type phytase, a commercially available phytase, or no phytase, comprises an increase in yeast cell count that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values. In some embodiments, the improved efficiency compared to a wild-type phytase, a commercially available phytase, or no phytase, comprises an increase in yeast budding that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values. In some embodiments, the improved efficiency compared to a wild-type phytase, a commercially available phytase, or no phytase, comprises an increase in yeast viability that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values.

In some embodiments, the improved efficiency compared to a wild-type phytase, a commercially available phytase, or no phytase, comprises an increase in ethanol yield that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values. In some embodiments, the improved efficiency compared to a wild-type phytase, a commercially available phytase, or no phytase, comprises a decrease in glycerol levels that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values. In some embodiments, the improved efficiency compared to a wild-type phytase, a commercially available phytase, or no phytase, comprises a decrease in total sugar levels that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values.

In some embodiments, the improved efficiency compared to a wild-type phytase, a commercially available phytase, or no phytase, comprises a decrease in fouling rate that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values. In some embodiments, the improved efficiency compared to a wild-type phytase, a commercially available phytase, or no phytase, comprises an increase in phosphorus levels that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values. In some embodiments, the improved efficiency compared to a wild-type phytase, a commercially available phytase, or no phytase, comprises an increase in operation time that is, is about, or is more than, 1%, 2%, 3%, 4%, 5%, 6%, 7%, 8%, 9%, 10%, 20%, 30%, 40%, 50%, 60%, 70%, 80%, 90%, or a range between any two of the above mentioned values.

Polypeptides with phytase activity disclosed herein can be added to ethanol processing equipment and/or processing fluid at a time point and under conditions required for the particular type of equipment or stage of ethanol processing. For example, phytases as disclosed herein can be used in any step of an alcohol product process as illustrated in FIG. 1.

In some embodiments, the variant polypeptide with phytase activity is added to any of the following: a feedstock, a hammer mill, a slurry tank, a jet cooker, a liquefaction, a mash cooker, a yeast mix tank, a yeast propagator, a fermentation tank, a beer, a distillation system, a whole stillage, a centrifuge, a thin stillage, an evaporator, a condensate, a syrup, a wet grain, a drum dryer, a dried distiller's grains with solubles, a condensed distiller's solubles, a dried distiller's grain, a wet distiller's grains with solubles, or any combination thereof.

In some embodiments, the phytase is added to the ethanol processing fluid at temperatures of about 20° C. to about 80° C., for example, about 20° C. to about 77° C., about 40° C. to about 65° C., or about 30° C. to about 55° C. (e.g., 52° C.). In an aspect, the phytase is added to the ethanol processing fluid at temperatures sufficient to allow the reaction between phytate and phytase to proceed to completion without degrading the enzyme. In another aspect, the phytase is added to the ethanol processing fluid at pH of about 3 to about 9, for example, about 4.0 to about 5.0, about 4.0 to about 5.5, or about 4.0 to about 5.3. In yet another aspect, the phytase is added at a pH of 4.0, and the reaction is conducted at temperatures of about 40° C. to about 65° C., about 20° C. to about 77° C., or about 30° C. to about 55° C. (e.g., 52° C.).

In some embodiments, the variant polypeptide is added to the ethanol processing fluids at a concentration of about 0.01 gallons per propagator up to about 10 gallons per propagator, or 0.1 gallons to 5 gallons per propagator, or 0.5 gallons to 2.5 gallons per propagator. In some embodiments the variant polypeptide is added at 0.01, 0.05, 0.1, 0.25, 0.5, 0.75, 1, 1.5, 2, 3, 4, 5, 6, 7, 8, 9, or 10 gallons per propagator.

In an embodiment, the variant polypeptide is added to ethanol processing fluids at lower concentrations, and the reaction is allowed to proceed over longer periods of time. Extending the reaction time or residence time allows smaller amounts of enzymes to be used, making ethanol processing more economical. In an aspect, the variant polypeptide is added to the ethanol processing fluids for a residence time sufficient for complete reaction of the variant polypeptide with the insoluble phytate. In another aspect, the variant polypeptide is added for a residence time of about 2 minutes to about 1200 minutes, for example, about 3 minutes to about 200 minutes, or about 3 minutes to about 40 minutes.

Polypeptides with phytase activity disclosed herein can be used in processing distillers dried grains for alcohol production—alcohol as in "spirits", e.g., beer or whiskey production (in addition to use in processing biomass for making biofuels). Phytases of this disclosure can be used in ethanol plants, e.g. for processing grains such as corn. Distillers dried grains can be made by first grinding a grain (e.g., corn) to a coarse consistency and adding to hot water. After cooling, yeast is added and the mixture ferments for several days to a week. The solids remaining after fermentation are the distillers grains. Phytases as disclosed herein may be used at any step of this process.

Polypeptides disclosed herein can be used for the processing of a biomass or any lignocellulosic material (e.g., any composition comprising a cellulose, hemicellulose and lignin) to a fuel (e.g., a bioethanol, biopropanol, biobutanol, biopropanol, biomethanol, biodiesel), in addition to feeds, foods and chemicals. For example, in one aspect, an enzyme as disclosed hereinbreaks down undigestable phytic acid (phytate) in a biomass (e.g., a lignocellulosic material, a grain or an oil seed) to release digestible phosphorus; thus, in one embodiment, phytases as disclosed herein are used to treat or pretreat a biomass.

Thus, the compositions and methods of the invention can be used in the production and/or processing of biofuels, e.g., to provide effective and sustainable alternatives and/or adjuncts to use of petroleum-based products; for example, compositions and methods as disclosed herein can be used with a mixture of enzymes to produce a biofuel—such as biomethanol, bioethanol, biopropanol, biobutanol, biodiesel and the like; which can be added to a diesel fuel, a gasoline, a kerosene and the like. Some embodiments disclosed herein provide organisms expressing enzymes of the invention for participation in chemical cycles involving natural biomass conversion. In one aspect, enzymes and methods for the conversion are used in enzyme ensembles for the efficient processing of biomass in conjunction with the depolymerization of polysaccharides, cellulosic and/or hemicellulosic polymers to metabolizeable (e.g., fermentable) carbon moieties. Some embodiments disclose methods for discovering and implementing the most effective of enzymes to enable these important new “biomass conversion” and alternative energy industrial processes.

The polypeptides and methods of the invention can be used to provide effective and sustainable alternatives or adjuncts to use of petroleum-based products, e.g., as a mixture of bioethanol, biopropanol, biobutanol, biopropanol, biomethanol and/or biodiesel and gasoline. In some embodiments, organisms are provided expressing enzymes for participation in chemical cycles involving natural biomass conversion. Some embodiments provide methods for discovering and implementing the most effective of enzymes to enable these important new “biomass conversion” and alternative energy industrial processes.

Some embodiments disclose methods, enzymes and mixtures of enzymes or “cocktails” of the invention, for processing a material, e.g. a biomass material, e.g., compositions comprising a cello-oligosaccharide, an arabinoxylan oligomer, a lignin, a lignocellulose, a xylan, a glucan, a cellulose and/or a fermentable sugar; e.g., including methods comprising contacting the composition with a polypeptide of the invention, or a polypeptide encoded by a nucleic acid disclosed herein, wherein optionally the material is derived from an agricultural crop (e.g., wheat, barley, potatoes, switchgrass, poplar wood), is a byproduct of a food or a feed production, is a lignocellulosic waste product, or is a plant residue or a waste paper or waste paper product, and optionally the plant residue comprise stems, leaves, hulls, husks, corn or corn cobs, corn stover, corn fiber, hay, straw (e.g. rice straw or wheat straw), sugarcane bagasse, sugar beet pulp, citrus pulp, and citrus peels, wood, wood thinnings, wood chips, wood pulp, pulp waste, wood waste, wood shavings and sawdust, construction and/or demolition wastes and debris (e.g. wood, wood shavings and sawdust), and optionally the paper waste comprises discarded or used photocopy paper, computer printer paper, notebook paper, notepad paper, typewriter paper, newspapers, magazines, cardboard and paper-based packaging materials, and recycled paper materials. In addition, urban wastes, e.g. the paper fraction of municipal solid waste, municipal wood waste, and municipal green waste, along with other materials containing sugar, starch, and/or cellulose can be used. In alternative embodiments, the processing of the material, e.g. the biomass material, generates a bioalcohol, e.g., a biodiesel, bioethanol, biomethanol, biobutanol or biopropanol.

The methods disclosed herein may also include taking the converted lignocellulosic material (processed by enzymes of the invention) and making it into a fuel (e.g. a bioalcohol, e.g., a bioethanol, biomethanol, biobutanol or biopropanol, or biodiesel) by fermentation and/or by chemical synthesis. In one aspect, the produced sugars are fermented and/or the non-fermentable products are gasified.

The methods disclosed herein also include converting algae, virgin vegetable oils, waste vegetable oils, animal fats and greases (e.g. tallow, lard, and yellow grease), or sewage, using enzymes of the invention, and making it into a fuel (e.g. a bioalcohol, e.g., a bioethanol, biomethanol, biobutanol or biopropanol, or biodiesel) by fermentation and/or by chemical synthesis or conversion.

The enzymes disclosed herein (including, for example, organisms, such as microorganisms, e.g., fungi, yeast or bacteria, making and in some aspects secreting recombinant enzymes as disclosed herein) can be used in or included/integrated at any stage of any biomass conversion process, e.g., at any one step, several steps, or included in all of the steps, or all of the following methods of biomass conversion processes, or all of these biofuel alternatives:

Direct combustion: the burning of material by direct heat and is the simplest biomass technology; can be very economical if a biomass source is nearby.

Pyrolysis: is the thermal degradation of biomass by heat in the absence of oxygen. In one aspect, biomass is heated to a temperature between about 800 and 1400 degrees Fahrenheit, but no oxygen is introduced to support combustion resulting in the creation of gas, fuel oil and charcoal.

Gasification: biomass can be used to produce methane through heating or anaerobic digestion. Syngas, a mixture of carbon monoxide and hydrogen, can be derived from biomass.

Landfill Gas: is generated by the decay (anaerobic digestion) of buried garbage in landfills. When the organic waste decomposes, it generates gas consisting of approximately 50% methane, the major component of natural gas.

Anaerobic digestion: converts organic matter to a mixture of methane, the major component of natural gas, and carbon dioxide. In one aspect, biomass such as waterwaste (sewage), manure, or food processing waste, is mixed with water and fed into a digester tank without air.

Fermentation Alcohol Fermentation: fuel alcohol is produced by converting cellulosic mass and/or starch to sugar, fermenting the sugar to alcohol, then separating the alcohol water mixture by distillation. Feedstocks such as dedicated crops (e.g., corn, wheat, barley, potatoes, switchgrass, *Miscanthus*, poplar wood), agricultural residues and wastes (e.g. rice straw, corn stover, wheat straw, sugarcane bagasse, rice hulls, corn fiber, sugar beet pulp, citrus pulp, and citrus peels), forestry wastes (e.g. hardwood and softwood thinnings, hardwood and softwood residues from timber operations, wood shavings, and sawdust), urban wastes (e.g. paper fraction of municipal solid waste, municipal wood waste, municipal green waste), wood wastes (e.g. saw mill waste, pulp mill waste, construction waste, demolition waste, wood shavings, and sawdust), and waste paper or other materials containing sugar, starch, and/or cellulose can be converted to sugars and then to alcohol by fermentation with yeast. Alternatively, materials containing sugars can be converted directly to alcohol by fermentation.

Transesterification: An exemplary reaction for converting oil to biodiesel is called transesterification. The transesterification process reacts an alcohol (like methanol) with the triglyceride oils contained in vegetable oils, animal fats, or recycled greases, forming fatty acid alkyl esters (biodiesel) and glycerin. The reaction requires heat and a strong base catalyst, such as sodium hydroxide or potassium hydroxide.

Biodiesel: Biodiesel is a mixture of fatty acid alkyl esters made from vegetable oils, animal fats or recycled greases. Biodiesel can be used as a fuel for vehicles in its pure form, but it is usually used as a petroleum diesel additive to reduce levels of particulates, carbon monoxide, hydrocarbons and air toxics from diesel-powered vehicles.

Hydrolysis: includes hydrolysis of a compound, e.g., a biomass, such as a lignocellulosic material, catalyzed using an enzyme as disclosed herein.

Cogeneration: is the simultaneous production of more than one form of energy using a single fuel and facility. In one aspect, biomass cogeneration has more potential growth than biomass generation alone because cogeneration produces both heat and electricity.

In one aspect, the polypeptides as disclosed herein can be used in conjunction with other enzymes, e.g., hydrolases or enzymes having alpha-amylase, glucoamylase, protease, xylanase, pullanase, cellulolytic activity, e.g., a glucanase, endoglucanase, mannase and/or other enzyme, for generating a fuel such as a bioalcohol, e.g., a bioethanol, biomethanol, biobutanol or biopropanol, or biodiesel, from any organic material, e.g., a biomass, such as compositions derived from plants and animals, including any agricultural crop or other renewable feedstock, an agricultural residue or an animal waste, the organic components of municipal and industrial wastes, or construction or demolition wastes or debris, or microorganisms such as algae or yeast.

In one aspect, polypeptides as disclosed herein are used in processes for converting lignocellulosic biomass to a fuel (e.g. a bioalcohol, e.g., a bioethanol, biomethanol, biobutanol or biopropanol, or biodiesel), or otherwise are used in processes for hydrolyzing or digesting biomaterials such that they can be used as a fuel (e.g. a bioalcohol, e.g., a bioethanol, biomethanol, biobutanol or biopropanol, or biodiesel), or for making it easier for the biomass to be processed into a fuel.

In one aspect, polypeptides disclosed herein, including the mixture of enzymes or "cocktails", are used in processes for a transesterification process reacting an alcohol (like ethanol, propanol, butanol, propanol, methanol) with a triglyceride oil contained in a vegetable oil, animal fat or recycled greases, forming fatty acid alkyl esters (biodiesel) and glycerin. In one aspect, biodiesel is made from soybean oil or recycled cooking oils, animal fats, other vegetable oils, and other recycled oils can also be used to produce biodiesel, depending on their costs and availability. In another aspect, blends of all kinds of fats and oils are used to produce a biodiesel fuel.

In some embodiments, the enzymes, including the mixture of enzymes or "cocktails", and methods disclosed herein can be used in conjunction with more "traditional" means of making ethanol, methanol, propanol, butanol, propanol and/or diesel from biomass, e.g., as methods comprising hydrolyzing lignocellulosic materials by subjecting dried lignocellulosic material in a reactor to a catalyst comprised of a dilute solution of a strong acid and a metal salt; this can lower the activation energy, or the temperature, of cellulose hydrolysis to obtain higher sugar yields as described in U.S. Pat. Nos. 6,660,506 and 6,423,145, the contents of which are hereby incorporated by reference in their entireties.

Mixtures or "cocktails" may include the polypeptides disclosed herein with other enzyme types, including glucanases, (or cellulases), mannanases, xylanases, amylases, xanthanases and/or glycosidases, e.g., cellobiohydrolases, mannanases and/or beta-glucosidases can be used in the conversion of biomass to fuels, and in the production of ethanol, e.g., as described in PCT Application Nos. WO0043496 and WO8100857, the contents of which are hereby incorporated by reference in their entireties. Enzymes that may be used with the enzymes disclosed herein include an amylase, a glucoamylase, a glucanase, a cellulase, an endoglucanase, a mannase, a xylanase, a xanthanase, a glycosidases, a cellobiohydrolase, a beta-glucosidase, a pullanase, a glucoisomerase, an alpha-glucosidase, or a combination thereof, and the like can be used in combination with phytase (e.g., enzymes) to convert starch to fermentable sugars or ethanol as described in PCT Application No. WO2005/096804, the content of which is hereby incorporated by reference in its entirety.

Another exemplary method that incorporates use of enzymes as disclosed herein, including the mixture of enzymes or "cocktails", comprises hydrolyzing a biomass, including any lignocellulosic material, e.g., containing hemicellulose, cellulose and lignin, or any other polysaccharide that can be hydrolyzed, by subjecting the material to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose as described in U.S. Pat. No. 5,536,325, the content of which is hereby incorporated by reference in its entirety. Enzymes disclosed herein (including disclosed mixtures, or "cocktails" of enzymes) can be added at any stage of this exemplary process.

In another aspect, methods are disclosed for producing biofuels (including bioalcohols such as bioethanols, biomethanols, biobutanols or biopropanols, or biodiesels) from a cellulosic substrate comprise providing a reaction mixture in the form of a slurry comprising cellulosic substrate, an enzyme as disclosed herein and a fermentation agent (e.g., within a reaction vessel, such as a semi-continuously solids-fed bioreactor), and the reaction mixture is reacted under conditions sufficient to initiate and maintain a fermentation reaction (as described, e.g., in U.S. Pat. App. No. 20060014260, the content of which is hereby incorporated by reference in its entirety). In one aspect, experiment or theoretical calculations can determine an optimum feeding frequency. In one aspect, additional quantities of the cellulosic substrate and the enzyme are provided into the reaction vessel at an interval(s) according to the optimized feeding frequency.

One exemplary process for making biofuels (including bioalcohols such as bioethanols, biomethanols, biobutanols or biopropanols, or biodiesels) is described in U.S. Pat. App. Pub. Nos. 20050069998; 20020164730, the content of which is hereby incorporated by reference in its entirety; and in one aspect comprises stages of grinding the lignocellulosic biomass (e.g., to a size of 15-30 mm), subjecting the product obtained to steam explosion pre-treatment (e.g., at a temperature of 190-230° C.) for between 1 and 10 minutes in a reactor; collecting the pre-treated material in a cyclone or related product of manufacture; and separating the liquid and solid fractions by filtration in a filter press, introducing the solid fraction in a fermentation deposit and adding one or more enzymes, e.g., a cellulase and/or beta-glucosidase enzyme (e.g., dissolved in citrate buffer pH 4.8).

Another exemplary process for making biofuels (including bioalcohols such as bioethanols, biomethanols, biobutanols or biopropanols, or biodiesels) comprising bioethanols, biomethanols, biobutanols or biopropanols using enzymes disclosed herein comprises pretreating a starting material comprising a lignocellulosic feedstock comprising at least hemicellulose and cellulose. In one aspect, the starting material comprises potatoes, soybean (rapeseed), barley, rye, corn, oats, wheat, beets or sugar cane or a component or waste or food or feed production byproduct. In some embodiments, the feedstock is selected from the from the group consisting of: corn, wheat, barley, potatoes, switchgrass, *Miscanthus*, poplar wood, rice straw, corn stover, wheat straw, sugarcane bagasse, rice hulls, corn fiber, sugar beet pulp, citrus pulp, citrus peels, hardwood, softwood thinnings, hardwood and softwood residues from timber operations, wood shavings, sawdust, paper fraction of municipal solid waste, municipal wood waste, municipal green waste, saw mill waste, pulp mill waste, construction waste, demolition waste, wood shavings, sawdust, waste paper, materials containing sugar, starch, and cellulose.

The starting material ("feedstock") is reacted at conditions which disrupt the plant's fiber structure to effect at least a partial hydrolysis of the hemicellulose and cellulose. Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent.

Exemplary conditions for using enzymes as disclosed herein in the hydrolysis of lignocellulosic material include reactions at temperatures between about 30° C. and 48° C., and/or a pH between about 4.0 and 6.0. Other exemplary conditions include a temperature between about 30° C. and 60° C. and a pH between about 4.0 and 8.0.

EXAMPLES

The examples which follow illustrate aspects of the present disclosure. The percentages in the examples are by weight, unless otherwise stated.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1: The Addition of Variant Polypeptides with Phytase Activity to Fermentation Processes May Lead to Increased Yeast Cell Counts, Yeast Budding, or Yeast Viability The effect of variant polypeptides with phytase activity on yeast cell counts, yeast budding, and yeast viability during the fermentation process is tested as follows. First, a feedstock consisting of whole corn or corn kernels is ground into meal through the use of a hammermill or equivalent. Water is then slurried with the meal to form a "mash" in a slurry tank. To minimize bacterial growth during the later fermentation phase, a high-temperature cooker such as a jet cooker is then used to process the mash and to reduce the levels of bacteria in the mash. This slurry is then pumped into liquefaction tanks. The corn starch in the mash gelatinizes and is degraded into shorter sugar chains (such as dextrins) by the addition of enzymes, including α-amylases. The pH of the mash is carefully monitored and adjusted through the addition of a carefully calculated amount of ammonia. This ammonia serves as a nitrogen source for yeast in a later step. To minimize bacterial growth during the later fermentation phase, a high-temperature cooker such as a jet cooker is then used to process the mash and to reduce the levels of bacteria in the mash.

After the transfer of the mash to the fermentation tanks, the fermentation tanks are divided into four different fermentation categories. The first fermentation category includes fermentation tanks that each have a specific type of variant phytase polypeptide added. These variant phytase polypeptides include those with substantial similarity to SEQ ID NO: 2, SEQ ID NO: 3, or a variant phytase polypeptide as disclosed herein. The second type of fermentation category includes fermentation tanks where the commercially available phytase Novozyme 50161 is added. The third type of fermentation category includes fermentation tanks where the commercially available phytase PhytOUT is added. The fourth type of fermentation category is a control group of fermentation tanks where no phytase enzyme is added. The three categories of phytases (variant polypeptides, Novozyme 50161, and U.S. Water PhytOUT) are each be mixed with yeast and glucoamylases in carefully separated yeast propagators and added jointly when the yeast is added to the fermentation tanks after the mash has been transferred in. Alternatively, the phytases are added after the yeast has been added to the fermentation tanks. Once the mash has been transferred into the fermentation tanks and yeast has been added, the fermentation process begins. As a part of the fermentation process, the sugars in the mash are converted to ethanol and carbon dioxide ($CO_2$). Byproducts of this process include glycerol and other products.

Although the industrial fermentation process usually runs for about 40 to 50 hours, for these comparison tests, the fermentation process are run for a shorter or longer period of time as necessary. During this time period, samples of the ethanol processing fluid and yeast mixtures are taken at regular and/or consistent time points. These samples are used to measure yeast cell counts, yeast budding, and yeast viability over time.

Yeast cell counts are measured using any generally accepted method, including but not limited to the use of hemocytometers, counting chambers, microscope-based counting methods, electronic counting methods, automated counting techniques, or any manual or automated cell counting device or machinery (such as a Coulter counter). Yeast viability is calculated using any generally accepted method, such as through 1) staining (e.g. methylene blue) to distinguish viable and non-viable yeast cells, 2) cell counting of viable and non-viable cells and the following formula: 3) Yeast Viability %=[(Total counted cells−Total counted non-viable cells)/Total counted cells]×100. Yeast budding percentage are calculated by counting budding yeast cells, while carefully distinguishing yeast cell buds emerging from mother cells as separate cells if the buds are at least one-half the size of the mother cell. The budding yeast cell counts are combined with the viable cell counts to determine the yeast budding % using the following formula: Yeast Budding %=(Total budding cells/Total viable cells)×100.

The timed samples from the three categories of phytase treated fermentation tanks and the control non-phytase treated fermentation tanks are then compared against each other for yeast cell counts, yeast budding percentage, and yeast viability. From these comparisons, the addition of the variant phytase polypeptides with phytase activities to a fermentation process may demonstrate increased yeast cell counts, yeast budding percentage, or yeast viability as compared with the non-phytase treated fermentation tanks as well as the Novozyme 50161 treated tanks and the PhytOUT treated tanks.

Example 2: Addition of Variant Polypeptides with Phytase Activity to Fermentation Processes May Increase Ethanol Yields, Decrease Glycerol Levels, or Decrease Total Sugar Levels The effect of variant polypeptides with phytase activity on ethanol yield, glycerol levels, and total sugar levels during the fermentation process are tested as follows. First, a feedstock consisting of whole corn or corn kernels is ground into meal through the use of a hammermill or equivalent. Water is then slurried with the meal to form a "mash" in a slurry tank. To minimize bacterial growth during the later fermentation phase, a high-temperature cooker such as a jet cooker is then used to process the mash and to reduce the levels of bacteria in the mash. This slurry is then pumped into liquefaction tanks. The corn starch in the mash gelatinizes and is degraded into shorter sugar chains (such as dextrins) by the addition of enzymes, including α-amylases. The pH of the mash is carefully monitored and adjusted through the addition of a carefully calculated amount of ammonia. This ammonia also serves as a nitrogen source for yeast in a later step.

After the transfer of the mash to the fermentation tanks, the fermentation tanks is divided into four different fermentation categories. The first fermentation category includes fermentation tanks that each have a specific type of variant phytase polypeptide added. These variant phytase polypeptides include those with substantial similarity to SEQ ID NO: 2, SEQ ID NO: 3, or a variant phytase polypeptide as disclosed herein. The second type of fermentation category includes fermentation tanks where the commercially available phytase Novozyme 50161 is added. The third type of fermentation category includes fermentation tanks where the commercially available phytase PhytOUT is added. The fourth type of fermentation category is a control group of fermentation tanks where no phytase enzyme is added. The three categories of phytases (variant phytase polypeptides, Novozyme 50161, and U.S. Water PhytOUT) are each mixed with yeast and glucoamylases in carefully separated yeast propagators and added jointly when the yeast is added to the fermentation tanks after the mash has been transferred in. Alternatively, the phytases are added after the yeast has been added to the fermentation tanks. Once the mash has been transferred into the fermentation tanks and yeast has been added, the fermentation process begins. As a part of the fermentation process, the sugars in the mash are converted to ethanol and carbon dioxide ($CO_2$). Byproducts of this process include glycerol and other products.

Although the industrial fermentation process usually runs for about 40 to 50 hours, for these comparison tests, the fermentation process may run for a shorter or longer period of time as necessary. During this time period, samples of the ethanol processing fluid and yeast mixtures are taken at regular and/or consistent time points. These samples are then be used to measure ethanol yield, glycerol levels, and total sugar levels over time.

Ethanol yields are measured using densitometry, ebulliometry, high performance liquid spectrometry (HPLC), gas chromatography, infrared spectrometry (IR), Fourier transform infrared spectroscopy (FTIR), or any other generally accepted method. The use of HPLC, gas chromatography, IR, or FTIR is preferred, as these techniques also facilitate the measurement of glycerol and total sugar levels. The timed samples from the three categories of phytase treated fermentation tanks and the control non-phytase treated fermentation tanks are then compared against each other for ethanol yield, glycerol levels, and total sugar levels. From these comparisons, the addition of the variant polypeptides with phytase activities may demonstrate an improvement in increased ethanol yield, decreased glycerol levels, or decreased sugar levels as compared with the non-phytase treated fermentation processes as well as the Novozyme 50161 treated and the PhytOUT treated fermentation processes.

Example 3: Addition of Variant Polypeptides with Phytase Activity Leads to a Decrease in Fouling Rates The effect of variant polypeptides with phytase activity on fouling rates during the fermentation process are tested as follows. First, a feedstock consisting of whole corn or corn kernels is ground into meal through the use of a hammermill or equivalent. Water is then slurried with the meal to form a "mash" in a slurry tank. To minimize bacterial growth during the later fermentation phase, a high-temperature cooker such as a jet cooker is then used to process the mash and to reduce the levels of bacteria in the mash. This slurry is then pumped into liquefaction tanks. The corn starch in the mash gelatinizes and is degraded into shorter sugar chains (such as dextrins) by the addition of enzymes, including α-amylases. The pH of the mash is carefully monitored and adjusted through the addition of a carefully calculated amount of ammonia. This ammonia also serves as a nitrogen source for yeast in a later step. To minimize bacterial growth during the later fermentation phase, a high-temperature cooker such as a jet cooker is then used to process the mash and to reduce the levels of bacteria in the mash.

After the transfer of the mash to the fermentation tanks, the fermentation tanks are divided into four different fermentation categories. The first fermentation category includes fermentation tanks that each have a specific type of variant phytase polypeptide added. These variant phytase polypeptides include those with substantial similarity to SEQ ID NO: 2, SEQ ID NO: 3, or a variant phytase polypeptide as disclosed herein. The second type of fermentation category includes fermentation tanks where the commercially available phytase Novozyme 50161 is added. The third type of fermentation category includes fermentation tanks where the commercially available phytase PhytOUT is added. The fourth type of fermentation category is a control group of fermentation tanks where no phytase enzyme is added. The three categories of phytases (variant polypeptides, Novozyme 50161, and U.S. Water PhytOUT) are each mixed with yeast and glucoamylases in carefully separated yeast propagators and added jointly when the yeast is added to the fermentation tanks after the mash has been transferred in. Alternatively, the phytases are added after the yeast has been added to the fermentation tanks. Once the mash has been transferred into the fermentation tanks and yeast has been added, the fermentation process begins. As a part of the fermentation process, the sugars in the mash are converted to ethanol and carbon dioxide ($CO_2$). Byproducts of this process include glycerol and other products.

Although the industrial fermentation process usually runs for about 40 to 50 hours, for the fouling rate tests, the fermentation process may run for a shorter or longer period of time as necessary. However, as one significant difference from Examples 1 and 2, fouling rates are measured via two different approaches. In the first approach, fermentation tank inlet pressure is measured at regular and/or consistent time points. Measurements of increased inlet pressure are used generally as a proxy for increased fouling. After the desired time has been satisfied, the fermentation tank is opened and solid fouling deposits is then directly examined and compared. These deposits are then collected and air-dried. Following the drying process, the samples can be examined by X-ray Fluorescence (XRF) or similar technologies. Deposits will be particularly examined for phytate and phytate salt concentrations, as these deposits are most relevant to phytase activity.

The timed inlet pressure samples from the three categories of phytase and the physical examination of solid deposits from the three categories of phytase treated fermentation tanks and the control non-phytase treated fermentation tanks are compared against each other. From these comparisons, results may demonstrate that the addition of the variant polypeptides with phytase activities to a fermentation process show a decreased fouling rate as compared with the non-phytase fermentation process as well as the Novozyme 50161 and the PhytOUT treated fermentation processes.

Example 4: Addition of Variant Polypeptides with Phytase Activity Increases Phosphorus Levels The effect of variant polypeptides with phytase activity on phosphorus levels during the fermentation process is tested as follows. First, a feedstock consisting of whole corn or corn kernels is ground into meal through the use of a hammermill or equivalent. Water is slurried with the meal to form a "mash" in a slurry tank. To minimize bacterial growth during the later fermentation phase, a high-temperature cooker such as a jet cooker is then used to process the mash and to reduce the levels of bacteria in the mash. This slurry is then pumped into liquefaction tanks. The corn starch in the mash gelatinizes and is degraded into shorter sugar chains (such as dextrins) by the addition of enzymes, including α-amylases. The pH of the mash is carefully monitored and adjusted through the addition of a carefully calculated amount of ammonia. This ammonia also serves as a nitrogen source for yeast in a later step.

After the transfer of the mash to the fermentation tanks, the fermentation tanks are divided into four different fermentation categories. The first fermentation category includes fermentation tanks that each have a specific type of variant phytase polypeptide added. These variant phytase polypeptides include those with substantial similarity to SEQ ID NO: 2, SEQ ID NO: 3, or a variant phytase polypeptide as disclosed herein. The second type of fermentation category includes fermentation tanks where the commercially available phytase Novozyme 50161 is added. The third type of fermentation category includes fermentation tanks where the commercially available phytase PhytOUT is added. The fourth type of fermentation category is a control group of fermentation tanks where no phytase enzyme is added. The three categories of phytases (variant phytase polypeptides, Novozyme 50161, and U.S. Water PhytOUT) are each mixed with yeast and glucoamylases in carefully separated yeast propagators and added jointly when the yeast is added to the fermentation tanks after the mash has been transferred in. Alternatively, the phytases are added after the yeast has been added to the fermentation tanks. Once the mash has been transferred into the fermentation tanks and yeast has been added, the fermentation process begins. As a part of the fermentation process, the sugars in the mash are converted to ethanol and carbon dioxide ($CO_2$). Byproducts of this process include glycerol and other products.

Although the industrial fermentation process usually runs for about 40 to 50 hours, for these comparison tests, the fermentation process may run for a shorter or longer period of time as necessary. During this time period, samples of the ethanol processing fluid are taken at regular and/or consistent time points. These samples are used to measure phosphorus levels over time.

Phosphorus levels may be measured by mineral element content through atomic absorption spectrometry, ammonia molybdate-vanadate spectrophotometry, or any other generally accepted method. The timed samples from the three categories of phytase treated fermentation tanks and the control non-phytase treated fermentation tanks are compared against each other for phosphorus levels. From these comparisons, it may be demonstrated that the addition of the variant polypeptides with phytase activities show an improvement in phosphorus fermentation levels as compared with the non-phytase treated fermentation processes as well as the Novozyme 50161 treated and the PhytOUT treated fermentation processes.

Example 5: Addition of Variant Polypeptides with Phytase Activity Leads to an Increase in Ethanol Production Equipment Operation Times The effect of variant polypeptides with phytase activity on fouling rates during the fermentation process is tested as follows. First, a feedstock consisting of whole corn or corn kernels is ground into meal through the use of a hammermill or equivalent. Water is slurried with the meal to form a "mash" in a slurry tank. To minimize bacterial growth during the later fermentation phase, a high-temperature cooker such as a jet cooker is then used to process the mash and to reduce the levels of bacteria in the mash. This slurry is then pumped into liquefaction tanks. The corn starch in the mash gelatinizes and is degraded into shorter sugar chains (such as dextrins) by the addition of enzymes, including α-amylases. This ammonia also serves as a nitrogen source for yeast in a later step.

After the transfer of the mash to the fermentation tanks, the fermentation tanks are divided into four different fermentation categories. The first fermentation category includes fermentation tanks that each have a specific type of variant phytase polypeptide added. These variant phytase polypeptides include those with substantial similarity to SEQ ID NO: 2, SEQ ID NO: 3, or a variant phytase polypeptide as disclosed herein. The second type of fermentation category includes fermentation tanks where the commercially available phytase Novozyme 50161 is added. The third type of fermentation category includes fermentation tanks where the commercially available phytase PhytOUT is added. The fourth type of fermentation category is a control group of fermentation tanks where no phytase enzyme is added. The three categories of phytases (variant phytase polypeptides, Novozyme 50161, and U.S. Water PhytOUT) are each mixed with yeast and glucoamylases in carefully separated yeast propagators and added jointly when the yeast is added to the fermentation tanks after the mash has been transferred in. Alternatively, the phytases are added after the yeast has been added to the fermentation tanks. Once the mash has been transferred into the fermentation tanks and yeast has been added, the fermentation process begins. As a part of the fermentation process, the sugars in the mash are converted to ethanol and carbon dioxide ($CO_2$). Byproducts of this process include glycerol and other products.

For the operation time tests, the fermentation processes are allowed to run until cleaning, maintenance, or shutdown becomes desirable or necessary. Multiple runs are performed to confirm that differences in operation time are consistent. The continuous operation times from the three categories of phytase treated fermentation tanks and the control non-phytase treated fermentation tanks are compared against each other. From these comparisons, results may demonstrate that the addition of the variant polypeptides with phytase activities to a fermentation process show an increased operation time as compared with the non-phytase fermentation process as well as the Novozyme 50161 and the PhytOUT treated fermentation processes.

Example 6: The Addition of Variant Polypeptides with Phytase Activity to Fermentation Processes Leads to Increased Yeast Health and Increased Ethanol Conversion Efficiency Ethanol Production—Mash Preparation Process The effect of adding SEQ ID NO: 2 variant polypeptides with phytase activity on increased yeast health and increased ethanol conversion efficiency during the fermentation process was tested as follows. First, a feedstock consisting of whole corn was ground into meal through the use of a hammermill or equivalent. Water was then slurried with the meal to form a "mash" in a slurry tank. To minimize bacterial growth during the later fermentation phase, a high-temperature cooker such as a jet cooker was used to process the mash and to reduce the levels of bacteria in the mash. This mash was then pumped into liquefaction tanks. The corn starch in the mash gelatinizes and was degraded into shorter sugar chains (such as dextrins) by the addition of enzymes, including α-amylases. The pH of the mash was carefully monitored and adjusted through the addition of a carefully calculated amount of ammonia. This ammonia served as a nitrogen source for yeast in a later step.

Mash exiting the liquefaction vessel was transferred to two places; one was the propagation tank and the other was the fermenter. Both the propagation and fermentation are batch processes and were cleaned after each batch. A small percentage of the overall mash heading from liquefaction went into the propagator and was diluted with additional water. This mixture in the propagator tank was then inoculated with yeast (dry or cream). Auxiliary enzymes such as protease and the three categories of phytases (SEQ ID NO: 2 variant polypeptides, Novozyme 50161, and U.S. Water PhytOUT) were added at the propagation step. In addition, glucoamylase and antibiotics can also be added to the propagation step.

The start of the propagation occurred about 4-10 hours before a clean fermenter begins filling with mash. Transferring the propagated material to the fermenter was determined based on yeast cell counts, fermentation fill time, and volume of the fermenter. After 10-20% of the working volume of the fermenter is filled, the propagator was transferred or sent to the fermenter for fermentation. As the fermenter filled, glucoamylase was added in one of the following ways: first, all at once at the beginning of fermentation fill (slug dose); second, several times over the course of fermentation fill (multiple slug doses); or third and in most cases, the glucoamylase was added continuously throughout the fermentation fill. Auxiliary enzymes like additional phytases, fungal alpha-amylase, cellulase, and/or proteases were added directly to the fermenter usually as a slug dose. The fermenters were typically filed to 95%-98% of fermenter capacity. Fermentation time ranged from 45-65 hours. The fermented mash (beer) was then transferred to the beer well.

Ethanol Production—Fermentation

After the transfer of the mash to the fermentation tanks, the fermentation tanks were divided into four different fermentation categories. The first fermentation category included fermentation tanks that had a variant polypeptide with substantial similarity to SEQ ID NO: 2. The second type of fermentation category included fermentation tanks where the commercially available phytase Novozyme 50161 was added. The third type of fermentation category was fermentation tanks where the commercially available phytase U.S. Waters PhytOUT was added. The fourth type of fermentation category was a control group of fermentation tanks where no phytase enzyme was added. Once the mash was transferred into the fermentation tanks and yeast was added, the fermentation process began. As a part of the fermentation process, the sugars in the mash were converted to ethanol and carbon dioxide ($CO_2$). Byproducts of this process included glycerol and other products.

During the fermentation process, samples were taken from each of the four categories at the following times to measure ethanol yields, glycerol levels and total sugar levels: a first sample at approximately 8 hours, a second sample at approximately 11-14 hours, a third sample at approximately 20 hours, a fourth sample at approximately 30 hours, a fifth sample at approximately 40 hours, a sixth sample at approximately 50 hours, and a seventh example at approximately 60 hours. For the three phytase treated fermentation categories, an additional sample was taken at approximately 70 hours. An additional sample was taken at about 85 hours for the fermentation tanks treated with a variant polypeptide with substantial similarity to SEQ ID NO: 2. For yeast health measurements such as yeast cell counts, yeast budding, and yeast viability, samples were taken at the same time periods but the fifth sample was the last taken for all four fermentation categories.

Yeast Cell Counts and Yeast Viability

Although yeast cell counts dropped over time for all four categories, the SEQ ID NO: 2 variant polypeptide treated fermentations showed a far smaller decline in yeast cell counts. Beginning at about the ten-hour mark and proceeding until the last sample taken, the SEQ ID NO: 2 variant polypeptide treated fermentations showed consistently higher yeast cell retention when compared to the other categories (FIG. 2).

At the forty-hour mark, the SEQ ID NO: 2 variant polypeptide treated fermentations showed the highest yeast viability (FIG. 2). The other two phytase treated fermentations underperformed the non-phytase treated fermentations, although the difference was small. Further, the Novozyme 50161 treated fermentations showed a very high standard deviation in yeast viability by the last sample measurement, demonstrating that there was a significant amount of volatility in yeast viability. Such high volatility is problematic as it signified that yeast viability with the Novozyme treated fermentations was highly unpredictable from batch to batch.

Ethanol Yield, Glycerol Levels, and Total Sugar Levels

The SEQ ID NO: 2 variant polypeptide treated fermentations tied with the Novozyme 50161 treated fermentations for the highest ethanol yields but outperformed the Novozyme 50161 fermentations with lower total sugar levels and slightly lower glycerol levels (FIG. 3). As compared with the other two categories, it had similar total sugar levels and glycerol levels but outperformed those fermentation methods in the most important category, ethanol yields.

Phosphorus Levels

The phosphorus levels were measured by taking multiple phosphate sample measurements from all four types of fermentations. For the three phytase treated fermentations, 28 phosphate samples were taken. For the non-phytase treated fermentations, only 3 samples were taken. The average phosphorus level for the variant polypeptide treated fermentations was 2,039 ppm phosphate taken across all 28 samples, with an average fermentation time sample point of 28.3 hours. The Novozyme 50161 treated fermentations had an average phosphorus level of 1,814 ppm phosphate with an average sampling time of 21.5 hours. The PhytOUT treated fermentations had an average of 1603 ppm phosphate with an average sampling time of 26.6 hours. The non-phytase treated fermentations had fewer samples taken at a much higher average sampling time of 65 hours and had an average level of 944 ppm phosphate. Thus, the phosphorus levels of the variant polypeptide treated fermentations were meaningfully higher than all other tested fermentation categories.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

All publications, including patent documents and scientific articles, referred to in this application and the bibliography and attachments are incorporated by reference for the referenced materials and in their entireties for all purposes to the same extent as if each individual publication were individually incorporated by reference.

Citation of the above publications or documents is not intended as an admission that any of the foregoing is pertinent prior art, nor does it constitute any admission as to the contents or date of these publications or documents.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention. The various embodiments of the invention should be understood that they have been presented by way of example only, and not by way of limitation. Likewise, the various diagrams may depict an example architectural or other configuration for the invention, which is done to aid in understanding the features and functionality that can be included in the invention. The invention is not restricted to the illustrated example architectures or configurations, but can be implemented using a variety of alternative architectures and configurations. Additionally, although the invention is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the invention, whether or not such embodiments are described, and whether or not such features are presented as being a part of a described embodiment. Thus the breadth and scope of the invention should not be limited by any of the above-described exemplary embodiments.

Terms and phrases used in this document, and embodiments thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless apparent from the context or expressly stated otherwise. Similarly, a group of items linked with the conjunction "or" should not be read as requiring mutual exclusivity among that group, but rather should also be read as "and/or" unless it is apparent from the context or expressly stated otherwise. Furthermore, although items, elements or components of the invention may be described or claimed in the singular, the plural is contemplated to be within the scope thereof unless limitation to the singular is explicitly stated. For example, "at least one" may refer to a single or plural and is not limited to either. The presence of broadening words and phrases such as "one or more," "at least," "but not limited to", or other like phrases in some instances shall not be read to mean that the narrower case is intended or required in instances where such broadening phrases may be absent.

What is claimed is:

1. A method for improving efficiency of ethanol production by yeast, the method comprising:

(a) adding a phytase variant polypeptide comprising an amino acid sequence that has at least 95% sequence identity to the amino acid sequence as set forth in amino acid residues 23-434 of SEQ ID NO: 2 to an

SEQUENCE LISTING

```
Sequence total quantity: 3
SEQ ID NO: 1           moltype = DNA  length = 1323
FEATURE                Location/Qualifiers
misc_feature           216
                       note = n is a, c, g, or t
source                 1..1323
                       mol_type = other DNA
                       organism = Escherichia coli
SEQUENCE: 1
atgaaagcga tcttaatccc atttttatct cttctgattc cgttaacccc gcaatctgca  60
ttcgctcaga gtgagccgga gctgaagctg gaaagtgtgg tgattgtcag tcgtcatggt  120
gtgcgtgctc caaccaaggc cacgcaactg atgcaggatg tcaccccaga cgcatggcca  180
acctggccgg taaaactggg ttggctgaca ccgcgnggtg gtgagctaat cgcctatctc  240
ggacattacc aacgccagcg tctggtagcc gacggattgc tggcgaaaaa gggctgcccg  300
cagtctggtc aggtcgcgat tattgctgat gtcgacgagc gtacccgtaa aacaggcgaa  360
gccttcgccg ccgggctggc acctgactgt gcaataaccg tacataccca ggcagatacg  420
tccagtcccg atccgttatt taatcctcta aaaactggcg tttgccaact ggataacgcg  480
aacgtgactg acgcgatcct cagcagggca ggagggtcaa ttgctgactt taccgggcat  540
cggcaaacgg cgtttcgcga actggaacgg gtgcttaatt ttccgcaatc aaacttgtgc  600
cttaaacgtg agaaacagga cgaaagctgt tcattaacgc aggcattacc atcggaactc  660
aaggtgagcg ccgacaatgt ctcattaacc ggtgcggtaa gcctcgcatc aatgctgacg  720
gagatatttc tcctgcaaca agcacaggga atgccggagc cggggtgggg aaggatcacc  780
gattcacacc agtggaacac cttgctaagt ttgcataacg cgcaatttta tttgctacaa  840
cgcacgccag aggttgcccg cagccgcgcc accccgttat tggatttgat catggcagcg  900
ttgacgcccc atccaccgca aaaacaggcg tatggtgtga cattacccac ttcagtactg  960
tttattgccg gacacgatac taatctggca aatctcggcg gcgcactgga gctcaactgg  1020
acgcttcccg gtcagccgga taacacgccg ccaggtggtg aactggtgtt tgaacgctgg  1080
cgtcggctaa gcgataacag ccagtggatt caggtttcgc tggtcttcca gactttacag  1140
cagatgcgtg ataaaacgcc gctgtcatta aatacgccgc ccggagaggt gaaactgacc  1200
ctggcaggat gtgaagagcg aaatgcgcag ggcatgtgtt cgttggcagg ttttacgcaa  1260
atcgtgaatg aagcacgcat accggcgtgc agtttgagat ctcatcacca tcaccatcac  1320
taa                                                                1323

SEQ ID NO: 2           moltype = AA  length = 440
FEATURE                Location/Qualifiers
source                 1..440
                       mol_type = protein
                       organism = Escherichia coli
SEQUENCE: 2
MKAILIPFLS LLIPLTPQSA FAQSEPELKL ESVVIVSRHG VRAPTKATQL MQDVTPDAWP  60
TWPVKLGWLT PRGGELIAYL GHYQRQRLVA DGLLAKKGCP QSGQVAIIAD VDERTRKTGE  120
AFAAGLAPDC AITVHTQADT SSPDPLFNPL KTGVCQLDNA NVTDAILSRA GGSIADFTGH  180
RQTAFRELER VLNFPQSNLC LKREKQDESC SLTQALPSEL KVSADNVSLT GAVSLASMLT  240
EIFLLQQAQG MPEPGWGRIT DSHQWNTLLS LHNAQFYLLQ RTPEVARSRA TPLLDLIMAA  300
LTPHPPQKQA YGVTLPTSVL FIAGHDTNLA NLGGALELNW TLPGQPDNTP PGGELVFERW  360
RRLSDNSQWI QVSLVFQTLQ QMRDKTPLSL NTPPGEVKLT LAGCEERNAQ GMCSLAGFTQ  420
IVNEARIPAC SLRSHHHHHH                                              440

SEQ ID NO: 3           moltype = AA  length = 414
FEATURE                Location/Qualifiers
REGION                 1..414
                       note = synthetic construct
source                 1..414
                       mol_type = protein
                       organism = synthetic construct
SEQUENCE: 3
SDTAPAGFQL EKVVILSRHG VRAPTKMTQT MRNVTPHQWP EWPVKLGYIT PRGEHLISLM  60
GGFYRERFQQ QGLLPKDNCP TPDAVYVWTD VDQRTRKTGE AFLAGLAPQC DLAIHHQQNI  120
QQADPLFHPV KAGICSMNKS QTYAAVEKQA GTPIETLNQR YQASLALMSS VLDFPKSPYC  180
QQHNIGKLCD FSQAMPSRLA ISDDGNEVQL EGAVGLSSTL AEIFLLEYAQ GMPVVAWGNI  240
HNESQWKSLL NLHNAHFDLM SRTPYIAKHN GTPLLQAISN ALNPNATESK LPDISPDNKI  300
LFIAGHDTNI ANIGGMLGMN WTLPGQPDNT PPGGGLVFEL WQNPDNHQQY VAVKMIYQTM  360
DQLRNSEKLD LKSHPAGIVP IEIEGCENIG TDKLCQLDTF QKRVAQVIEP ACQI        414
```

ethanol processing fluid in an ethanol production facility, wherein the ethanol processing fluid comprises phytic acid, wherein the addition of the phytase variant polypeptide improves ethanol production efficiency comprising one or more of:

increased yeast cell count, yeast budding or yeast viability;

increased ethanol yield, decreased glycerol levels, or decreased total sugar levels;

decreased fouling rate;

increased phosphorous levels; and increased operation time of the ethanol production facility when compared to a production process wherein a wild-type phytase consisting of the amino acid sequence as set forth in amino acid residues 23-434 of SEQ ID NO: 2 is added to the ethanol processing liquid and, wherein the phytase variant polypeptide comprises at least one single amino acid substitution selected from the group consisting of W68E, Q84W, A95P, K97E, N159Q, T163P, R181Y, N226D and Y277D.

2. The method of claim 1, wherein the ethanol production facility comprises a feedstock, a hammer mill, a slurry tank, a jet cooker, a liquefaction, a mash cooker, a yeast mix tank, a yeast propagator, a fermentation tank, a beer, a distillation system, a whole stillage, a centrifuge, a thin stillage, an evaporator, a condensate, a syrup, a wet grain, a drum dryer, a dried distiller's grains with solubles, a condensed distiller's solubles, a dried distiller's grain, a wet distiller's grains with solubles, or any combination thereof.

3. The method of claim 1, wherein addition of the phytase variant polypeptide improves ethanol production efficiency compared to a production process where no phytase is added.

4. The method of claim 1, wherein addition of the phytase variant polypeptide improves ethanol production efficiency compared to a production process where a commercially available phytase is added, and wherein the commercially available phytase is selected from Novozyme 50161™ and U.S. Water PhytOUT™.

5. The method of claim 1, wherein the phytase variant polypeptide is added to the ethanol processing fluid prior to fermentation.

6. The method of claim 1, wherein the ethanol production facility comprises a mash cooker and the phytase variant polypeptide is added to the ethanol processing fluid in the mash cooker.

7. The method of claim 1, wherein the ethanol production facility comprises a yeast mix tank and a yeast propagator and the phytase variant polypeptide is added to the ethanol processing fluid in a yeast mix tank, and wherein the ethanol processing fluid proceeds from the yeast mix tank to a yeast propagator.

8. The method of claim 7, wherein the phytase variant polypeptide is added to the ethanol processing fluid at a dose of 0.5 gallons per yeast propagator.

9. The method of claim 1, wherein the operation time comprises one or both of beer/mash heat exchanger online time and beer feed pre-heater exchanger online time.

10. The method of claim 1, wherein the ethanol production facility is in an ethanol production plant; a spirit or a drinkable alcohol production plant; or a fuel ethanol plant.

11. The method of claim 2, wherein the feedstock is selected from the group consisting of: corn, wheat, barley, potatoes, switchgrass, *Miscanthus*, poplar wood, rice straw, corn stover, wheat straw, sugarcane bagasse, rice hulls, corn fiber, sugar beet pulp, citrus pulp, citrus peels, hardwood, softwood thinnings, hardwood and softwood residues from timber operations, wood shavings, sawdust, paper fraction of municipal solid waste, municipal wood waste, municipal green waste, saw mill waste, pulp mill waste, construction waste, demolition waste, waste paper, materials containing sugar, starch, and cellulose.

12. The method of claim 2, wherein the ethanol production facility comprises a fermentation tank and a distillation system, wherein said fermentation tank comprises yeast cells which convert sugar, starch, or cellulose to ethanol, and the ethanol produced in the fermentation tank is separated by the distillation system.

13. The method of claim 1, wherein the variant polypeptide hydrolyzes phytate to inositol and free phosphate with release of minerals from the phytic acid.

14. The method of claim 1, wherein the phytic acid is phytate in the form of calcium salts, magnesium salts, metal ions, proteins, unhydrolyzed phytate sludge, or myo-inositol-hexaphosphate.

15. The method of claim 1, wherein the variant polypeptide is used in combination with one or more other enzymes.

16. The method of claim 15, wherein the one or more other enzymes comprise an amylase, a glucoamylase, a glucanase, a cellulase, an endoglucanase, a mannase, a xylanase, a xanthanase, a glycosidases, a cellobiohydrolase, a beta-glucosidase, a pullanase, a glucoisomerase, an alpha-glucosidase, or a combination thereof.

17. The method of claim 1, wherein the variant polypeptide retains phytase activity under conditions from pH 2.5 to pH 12.0.

18. The method of claim 1, wherein the variant polypeptide further comprises at least one single amino acid substitution selected from the group consisting of: A47F, T48F, T48H, T48I, T48K, T48L, T48M, T48V, T48W, T48Y, L50W, M51A, M51G, M51L, G67A, Y79H, Y79N, Y79S, Y79W, Q86H, K97C, K97V, P100A, P102A, P102Y, I107H, I107P, I108A, I108Q, I108R, I108S, I108Y, A109V, E113P, L126R, T136H, Q137F, Q137L, Q137V, Q137Y, D139Y, P145L, L146R, L146T, F147Y, N148K, N148M, N148R, P149L, P149N, I150T, I150Y, K151H, K151P, C155Y, L157C, L157P, N159V, N161K, V162L, V162T, T163R, D164R, L167S, S168R, S168E, G171M, G171S, S173G, S173H, S173V, I174F, G179R, V191A, L192F, F194L, S197G, S208P, S211H, L216T, P217D, P217G, P217L, P217S, S218I, S218Y, N226C, A232P, V233W, Q275V, A236H, A236T, L244S, Q246W, Q247H, A248L, A248T, P254S, G257A, G257R, H263P, W265L, N266P, L269I, L269T, L269P, H272W, A274F, A274I, A274L, A274T, A274V, Q275V, T282H, R289A, T291V, T291W, L296T, M298K, A299T Q309P, N339E, T341D, P343E, P343I, P343L, P343N, P343R, P343V, N348K, N348W, T349Y, G353C, L363P, Q377R, L379S, L379V, Q381S, S389H, S389V, G395E, G395I, G395L, G395Q, G395T, V422M, I427G, I427S, I427T, A429P, and any combination thereof.

* * * * *